United States Patent [19]
Herbert et al.

[11] Patent Number: 5,654,008
[45] Date of Patent: Aug. 5, 1997

[54] PREPARATION OF BIODEGRADABLE MICROPARTICLES CONTAINING A BIOLOGICALLY ACTIVE AGENT

[75] Inventors: Paul F. Herbert, Wayland, Mass.; Azar M. Hazrati, Maineville, Ohio

[73] Assignee: Alkermes Controlled Therapeutics Inc. II, Cambridge, Mass.

[21] Appl. No.: 729,277

[22] Filed: Oct. 10, 1996

Related U.S. Application Data

[63] Continuation of Ser. No. 338,805, Nov. 10, 1994, abandoned, which is a continuation-in-part of Ser. No. 154,409, Nov. 19, 1993, abandoned, and Ser. No. 298,787, Aug. 31, 1994, abandoned.

[51] Int. Cl.$^6$ ............................... A61K 9/50; B01J 13/02
[52] U.S. Cl. ............... 424/489; 424/497; 264/41; 264/46; 427/213.3; 427/213.36
[58] Field of Search ............... 424/497; 264/4.1, 264/4.6; 427/213.3, 213.36

[56] References Cited

U.S. PATENT DOCUMENTS

| | | | |
|---|---|---|---|
| 3,197,180 | 7/1965 | Bates. | |
| 3,523,906 | 8/1970 | Vrancken et al. | 252/316 |
| 3,691,090 | 9/1972 | Kitajima et al. | 252/316 |
| 3,737,337 | 6/1973 | Schnoring et al. | 117/100 |
| 3,891,570 | 6/1975 | Fukushima et al. | 252/316 |
| 3,923,288 | 12/1975 | King | 259/4 |
| 3,960,757 | 6/1976 | Morishita et al. | 252/316 |
| 4,034,965 | 7/1977 | King | 259/4 |
| 4,111,402 | 9/1978 | Barbini | 366/338 |
| 4,201,482 | 5/1980 | Imhauser et al. | 366/98 |
| 4,208,136 | 6/1980 | King | 366/338 |
| 4,389,330 | 6/1983 | Tice et al. | 427/213.36 |
| 4,511,258 | 4/1985 | Federighi et al. | 366/337 |

(List continued on next page.)

FOREIGN PATENT DOCUMENTS

| | | |
|---|---|---|
| 0 071 454 | 2/1983 | European Pat. Off. . |
| 0 195 450 | 9/1986 | European Pat. Off. . |
| 1212730 | 11/1970 | United Kingdom . |
| 1351811 | 5/1974 | United Kingdom . |
| 2015360 | 9/1979 | United Kingdom . |
| 2120113 | 11/1983 | United Kingdom . |
| WO89/03678 | 5/1989 | WIPO . |
| 9013361 | 11/1990 | WIPO . |
| WO 94/10982 | 5/1994 | WIPO . |

OTHER PUBLICATIONS

Koch Engineering Company, Inc., "All Mixing Problems are Not Alike", 1 page, Product Brochure.
Koflo Corporation, "Static In-Line Mixers", 4 pages, Product Brochure.
Koch Engineering Company, Inc., "Static Mixing Technology" Article, pp. 1–15 (1991).
"Motionless Mixers Stir Up New Uses", Jim R. Baker Chemical Engineering Progress, pp. 32–38 (Jun. 1991).
"In-Line Dispersion and Mass Transfer Using Static Mixing Equipment", F. Strieff, Sulzer Technical Review, pp. 108–114 (1977).
"Advances In Static mixing Technology", M. Mutsakis, F.A. Streiff and G. Schneider, Chemical Engineering Progress, pp. 42–48 (Jul. 1986).
Komax Systems, Inc. "Triple Action Static mixers" 2 pages, Product Brochure.
Chemineer, Kenics Static Mixers, Bulletin 800, pp. 1–11 (1986).
Abstract of PCT Application no. WO 94/10982.

*Primary Examiner*—Amy Hulina
*Attorney, Agent, or Firm*—Sterne, Kessler, Goldstein & Fox P.L.L.C.

[57] ABSTRACT

A process for preparing biodegradable microparticles comprising a biodegradable polymeric binder and a biologically active agent. A first phase, comprising the active agent and the polymer, and a second phase are pumped through a static mixer into a quench liquid to form microparticles containing the active agent. Preferably, a blend of at least two substantially non-toxic solvents, free of halogenated hydrocarbons, is used to dissolve or disperse the agent and dissolve the polymer.

21 Claims, 15 Drawing Sheets

U.S. PATENT DOCUMENTS

| | | | |
|---|---|---|---|
| 4,574,110 | 3/1986 | Asnao et al. | 428/402.21 |
| 4,612,364 | 9/1986 | Yamamoto et al. | 528/491 |
| 4,614,440 | 9/1986 | King | 366/336 |
| 4,616,937 | 10/1986 | King | 366/336 |
| 4,643,584 | 2/1987 | Allocca | 366/337 |
| 4,668,580 | 5/1987 | Dahm et al. . | |
| 4,675,189 | 6/1987 | Kent et al. | 424/490 |
| 4,731,205 | 3/1988 | Mcnulty | 261/94 |
| 4,753,535 | 6/1988 | King | 366/337 |
| 4,765,204 | 8/1988 | Buchholz et al. | 76/101 |
| 4,793,713 | 12/1988 | King | 366/150 |
| 4,808,007 | 2/1989 | King | 366/337 |
| 4,936,689 | 6/1990 | Federighi et al. | 366/337 |
| 4,936,901 | 6/1990 | Surgant, Sr. et al. . | |
| 4,954,298 | 9/1990 | Yamamoto et al. | 264/46 |
| 4,978,483 | 12/1990 | Redding, Jr, . | |
| 5,061,410 | 10/1991 | Sakamoto et al. | 264/4.7 |
| 5,401,443 | 3/1995 | Nagano et al. | 264/4.7 |

PREPARATION OF BIODEGRADABLE MICROPARTICLES CONTAINING A BIOLOGICALLY ACTIVE AGENT

CROSS-REFERENCE TO RELATED APPLICATIONS

This application is a continuation of application Ser. No. 08/338,805, filed Nov. 10, 1994, which is a continuation in part of application Ser. No. 08/154,409, filed Nov. 19, 1993; and a continuation in part of application Ser. No. 08/298, 787, filed Aug. 31, 1994; all now abandoned.

BACKGROUND OF THE INVENTION

1. Field of the Invention

This invention relates to the preparation of microparticles. More particularly, the present invention relates to a method of encapsulating active agents to form controlled-release microparticles through the use of static mixers. The present invention also relates to a solvent system useful in a method of encapsulating active agents to form controlled-release microparticles. By "microparticles" or "microspheres" is meant solid particles that contain an active agent dispersed or dissolved within a biodegradable polymer that serves as the matrix of the particle.

2. Description of the Related Art

A variety of methods is known by which compounds can be encapsulated in the form of microparticles. It is particularly advantageous to encapsulate a biologically active or pharmaceutically active agent within a biocompatible, biodegradable, wall forming material (e.g., a polymer) to provide sustained or delayed release of drugs or other active agents. In these methods, the material to be encapsulated (drugs or other active agents) is generally dissolved, dispersed, or emulsified, using stirrers, agitators, or other dynamic mixing techniques, in a solvent containing the wall forming material. Solvent is then removed from the microparticles and thereafter the microparticle product is obtained.

An example of a conventional microencapsulation process is disclosed in U.S. Pat. No. 3,737,337 wherein a solution of a wall or shell forming polymeric material in a solvent is prepared. The solvent is only partially miscible in water. A solid or core material is dissolved or dispersed in the polymer-containing solution and, thereafter, the core-material-containing solution is dispersed in an aqueous liquid that is immiscible in the organic solvent in order to remove solvent from the microparticles. The substances to be encapsulated or embedded are dissolved or dispersed in the organic solution of the polymer (phase A), using conventional mixers including (in the preparation of a dispersion) vibrators, and high speed stirrers, etc. The dispersion of phase (A), containing the core material in solution or in suspension, is carried out in the aqueous phase (B) again using conventional mixers, such as high-speed mixers, vibration mixers or even spray nozzles, in which case the particle size of the microgranulates will be determined not only by the concentration of phase (A) but also by the particle sizes obtained.

Another example of a process in which solvent is removed from microparticles containing a substance is disclosed in U.S. Pat. No. 3,523,906. In this process, a material to be encapsulated is emulsified in a solution of a polymeric material in a solvent that is immiscible in water and then the emulsion is emulsified in an aqueous solution containing a hydrophilic colloid. Solvent removal from the microparticles is then accomplished by evaporation and the product is obtained.

In still another process, as disclosed in U.S. Pat. No. 3,691,090, organic solvent is evaporated from a dispersion of microparticles in an aqueous medium, preferably under reduced pressure.

Similarly, U.S. Pat. No. 3,891,570 discloses a method in which microparticles are prepared by dissolving or dispersing a core material in a solution of a wall material dissolved in a solvent having a dielectric constant of 10 or less and poor miscibility with a polyhydric alcohol, then emulsifying in fine droplets through dispersion or solution into the polyhydric alcohol and finally evaporating the solvent by the application of heat or by subjecting the microparticles to reduced pressure.

Another example of a process in which an active agent may be encapsulated is disclosed in U.S. Pat. No. 3,960,757. Encapsulated medicaments are prepared by dissolving a wall material for capsules in at least one organic solvent, poorly miscible with water, that has a boiling point of less than 100° C., a vapor pressure higher than that of water, and a dielectric constant of less than about 10; dissolving or dispersing a medicament that is insoluble or slightly soluble in water in the resulting solution; dispersing the resulting solution or dispersion to the form of fine drops in a liquid vehicle comprising an aqueous solution of a hydrophilic colloid or a surface active agent, and then removing the organic solvent by evaporation. The size of the fine drops is determined according to the stirring speed, the viscosity of the organic solvent solution containing the medicament and the wall material, and the viscosity and surface tension of the vehicle.

Tice et al. in U.S. Pat. No. 4,389,330 describe the preparation of microparticles containing an active agent by using a two-step solvent removal process. This two-step solvent removal process is advantageous because it results in microparticles having higher active agent loading and a higher quality than techniques in which solvent is removed in a single step. In the Tice et al. process, the active agent and the polymer are dissolved in a solvent. The mixture of ingredients in the solvent is then emulsified in a continuous-phase processing medium that is immiscible with the solvent. A dispersion of microparticles containing the indicated ingredients is formed in the continuous-phase medium by mechanical agitation of the mixed materials. From this dispersion, the organic solvent can be partially removed in the first step of the solvent removal process. After the first stage, the dispersed microparticles are isolated from the continuous-phase processing medium by any convenient means of separation. Following the isolation, the remainder of the solvent in the microparticles is removed by extraction. After the remainder of the solvent has been removed from the microparticles, they are dried by exposure to air or by other conventional drying techniques.

Tice et al., in U.S. Pat. No. 4,530,840, describe the preparation of microparticles containing an anti-inflammatory active agent by a method comprising: (a) dissolving or dispersing an anti-inflammatory agent in a solvent and dissolving a biocompatible and biodegradable wall forming material in that solvent; (b) dispersing the solvent containing the anti-inflammatory agent and wall forming material in a continuous-phase processing medium; (c) evaporating a portion of the solvent from the dispersion of step (b), thereby forming microparticles containing the anti-inflammatory agent in the suspension; and (d) extracting the remainder of the solvent from the microparticles.

WO 90/13361 discloses a method of microencapsulating an agent to form a microencapsulated product, having the steps of dispersing an effective amount of the agent in a solvent containing a dissolved wall forming material to form a dispersion; combining the dispersion with an effective amount of a continuous process medium to form an emulsion that contains the process medium and microdroplets having the agent, the solvent, and the wall forming material; and adding the emulsion rapidly to an effective amount of an extraction medium to extract the solvent from the microdroplets to form the microencapsulated product.

Bodmeier, R. et al., *International Journal of Pharmaceutics* 43:179–186 (1988), disclose the preparation of microparticles containing quinidine or quinidine sulfate as the active agent and poly(D,L-lactide) as the binder using a variety of solvents including methylene chloride, chloroform, and benzene as well as mixtures of methylene chloride and a water miscible liquid, such as acetone, ethyl acetate, methanol, dimethylsulfoxide, chloroform, or benzene to enhance drug content.

Beck, L. R. et al., *Biology of Reproduction* 28:186–195 (1983), disclose a process for encapsulating norethisterone in a copolymer of D,L-lactide and glycolide by dissolving both the copolymer and the norethisterone in a mixture of chloroform and acetone that is added to a stirred cold aqueous solution of polyvinyl alcohol to form an emulsion and the volatile solvents removed under reduced pressure to yield microcapsules.

Phase separation or non-solvent induced coacervation is a method which has also been employed to prepare microparticles comprised of a biodegradable polymeric matrix and a biologically active agent. Many of the published procedures for microencapsulation with lactide/glycolide copolymers employ solvent evaporation/extraction techniques, but these techniques are mostly suitable for water insoluble drugs because water soluble drugs may partially partition into the aqueous phase during the preparation process. The phase separation method, utilizes non-solvents for the polymer and in which hydrophilic active agents also are not soluble, is an efficient method of encapsulation for these active agents.

In a conventional phase separation method, a known amount of polymer, such as poly(lactide-co-glycolide), PLGA, with a monomeric ratio of lactide to glycolide ranging from 100:0 to 50:50, is dissolved in an appropriate organic solvent. The solid drug, preferably lyophilized and micronized, may be dispersed in the polymer solution, where it is insoluble or slightly soluble in the organic solvent. Alternaltively, the active agent may be dissolved in water, or in water which contains some additives, and emulsified in the polymer solution, preferably mainly by sonication, forming a water-in-oil emulsion. The resultant suspension or emulsion is then added to a reactor and addition of a first non-solvent is initiated at a predetermined rate. A turbine mixer installed in the reactor is used to provide moderate mixing. At the completion of the phase separation process, the mixture is transferred into a quench tank containing a second non-solvent to solidify the semi-solid microspheres. The hardened microspheres are collected by sieving and are washed and stored in a vacuum oven for further drying.

Very often the solvents used in the known microencapsulation processes are halogenated hydrocarbons, particularly chloroform or methylene chloride, which act as solvents for both the active agent and the encapsulating polymer. The presence of small, but detectable, halogenated hydrocarbon residuals in the final product, however, is undesirable, because of their general toxicity and possible carcinogenic activity. Thus, a need exists to revise the known microencapsulation processes using less toxic and acceptable alternative solvents.

With conventional techniques for the microencapsulation of biological or pharmaceutical active agents, such as those described above, the microparticles form when the solvent containing an active agent and a polymer is emulsified or dispersed in an immiscible solution by stirring, agitating, vibrating, or some other dynamic mixing technique, often for a relatively long period of time. Such dynamic mixing techniques have several drawbacks. For example, it is difficult to control the size of the resulting microparticles, or the distribution of sizes obtained. As a consequence, use of dynamic mixing also presents problems when preparing microparticles containing biological or pharmaceutical agents on a production or commercial scale. Particularly, production equipment includes a costly emulsion tank, including equipment to stir or agitate the fluids. One of the controlling factors for overall process time is the time required to form a homogeneous (uniform) emulsion. Increased batch sizes in larger tanks require a longer time to form the emulsion, resulting in a longer overall production process time. Longer exposure times of the active agent to process solvents and to polymer solutions can lead to degradation or deactivation of the active agent. Scale-up to a production process from a laboratory emulsion process is particularly difficult for microencapsulation of biological or pharmaceutical agents since, as the batch and tank size are increased, stir speeds and viscosities within the larger tank have to be empirically optimized by trial and error at each stage of the scale-up. Likewise, the phase separation technique is not easily converted into a process for producing commercial scale quantities of microparticles because processing parameters, i.e., rate of non-solvent addition, agitation conditions, and the viscosity of both the active agent/polymer solution and the non-solvent must be empirically optimized by trial and error at each stage of scale-up. Thus, scale-up of conventional microencapsulation techniques is not only time consuming, but imprecise.

Tests were conducted in an attempt to scale-up a laboratory emulsion formation process from small stirred glass reactors to production equipment for microparticles containing estradiol benzoate. The shear created by the mixer blades determined the particle size of the emulsion; the higher the shear, the smaller the particles. Due to the low viscosity of the oil (organic) phase in the estradiol benzoate process, low shear is required to produce the large emulsion particles which were desired. In large reactors it is difficult to maintain low shear and still provide uniform mixing. The speed at which the agitator must turn to provide a uniform tank composition produces a small particle size with a broad distribution of sizes. Larger mixing blade diameters and multiple mixing blades, along the shaft helped to provide better mixing at low shear but still produced a very broad distribution of sizes. Particle size control became less reliable as batch size was increased.

Accordingly, one advantage of the method of preparing microparticles of the present invention is that accurate and reliable scaling from laboratory to commercial batch sizes can be done, while achieving a narrow and well defined size distribution of microparticles containing biologically or pharmaceutically active agents. This can be achieved for any suitable encapsulation technique including, but not limited to, solvent extraction and phase separation. A further advantage of the method of the present invention is that the same equipment can be used to form microparticles containing active agents of a well defined size distribution for varying batch sizes. Yet another advantage of the method of the present invention is that high quality microparticles having a high concentration of active agent can be obtained using a single step to remove solvent, or through a phase separation technique.

SUMMARY OF THE INVENTION

The present invention relates to a method of preparing microparticles.

More particularly, the present invention relates to a process for preparing biodegradable microparticles comprising a biodegradable polymeric binder and a biologically active agent. In one aspect of the invention, a first phase, comprising an active agent and a polymer, and a second phase are pumped through a static mixer into a quench liquid to form microparticles containing the active agent. In a further aspect of the invention, the first phase and the second phase are substantially immiscible. In another aspect of the invention, the second phase is free from solvents for the polymer and active agent, and may be comprised of an aqueous solution of an emulsifier. The process of the present invention whereby microparticles are prepared using static mixers can be used with any conventional encapsulation technique including, but not limited to, solvent extraction and phase separation.

In further aspects of the invention, the first phase is prepared by dissolving the active agent in a solution containing the polymer, by preparing a dispersion comprising the active agent, and by preparing an emulsion comprising the active agent.

In yet further aspects of the invention, the method is used to prepare microparticles containing the following active agents: risperidone; trenbolone acetate; norethindrone; testosterone; estrodiol benzoate; human serum albumin; pig albumin; and recombinant bovine interferon-alpha.

In a preferred embodiment of the invention, a blend of at least two substantially non-toxic solvents, free of halogenated hydrocarbons, is used to dissolve both the agent and the polymer. The solvent blend containing the dissolved agent and polymer is dispersed in an aqueous solution to form droplets. The resulting emulsion is then added to an aqueous extraction medium preferably containing at least one of the solvents of the blend, whereby the rate of extraction of each solvent is controlled, whereupon the biodegradable microparticles containing the biologically active agent are formed. The process has the advantages that less extraction medium is required because the solubility of one solvent in water is substantially independent of the other and solvent selection is increased, especially with solvents that are particularly difficult to extract.

In a preferred embodiment, the present invention relates to a solvent system useful in a method of preparing a pharmaceutical composition in microparticle form designed for the controlled release of an effective amount of a drug over an extended period of time. This composition comprises at least one pharmaceutical agent and at least one biocompatible, biodegradable encapsulating polymer.

More particularly, in yet a further aspect of the invention, the present invention relates to a method for preparing microparticles comprising:

A. preparing a first phase comprising a biodegradable polymeric encapsulating binder and an active agent dissolved or dispersed in a blend of at least two mutually miscible organic solvents free from halogenated hydrocarbons and having limited water solubility, B. preparing a second phase comprising an aqueous solution of (1) a hydrophilic colloid or
(2) a surfactant, C. combining said first phase and said second phase under the influence of mixing means to form an emulsion in which said first phase is discontinuous and said second phase continuous, and D. isolating said discontinuous first phase in the form of microparticles.

Limited water solubility means having a solubility in water in the range of from about 0.1 to about 25 wt. % at 20° C.

In a preferred embodiment, the present invention relates to a method for preparing microparticles comprising preparing a first "oil" phase containing from about 5 weight percent to about 50 weight percent solids of which from about 5 to about 95 weight percent is a solution of biodegradable polymeric encapsulating binder and and incorporating from about 5 to about 95 weight percent, as based on polymeric binder, of an active agent in a solvent blend, the blend comprising first and second mutually miscible solvents, free from halogenated hydrocarbons, each having a solubility in water of from about 0.1 to about 25 weight percent at 20° C., forming an emulsion containing from 1:1 to 1:10 of the first phase in an emulsion process medium to form microdroplets of the first phase composition in a continuous aqueous second phase processing medium, adding the combined first and second phases to an aqueous extraction quench liquid at a level of from about 0.1 to about 20 liters of aqueous quench liquid per gram of polymer and active agent, said quench liquid containing the solvent of the blend having the greater water solubility at a level of from about 20% to about 70% of the saturation level of that solvent in the quench liquid at the temperature being used, and recovering microparticles from the quench liquid.

In another aspect, the invention is directed to a method of preparing microparticles comprising the steps of: preparing a first phase, said first phase comprising a biologically active agent, a biodegradable polymer, and a blend of at least two mutually miscible solvents for the agent and the polymer free from halogenated hydrocarbons; preparing a second phase, wherein said first phase is substantially immiscible in said second phase; flowing said first phase through a static mixer at a first flow rate; flowing said second phase through said static mixer at a second flow rate so that said first phase and said second phase flow simultaneously through said static mixer thereby forming microparticles containing said active agent; and isolating said microparticles.

In another aspect, the invention is directed to a method of preparing microparticles comprising the steps of: preparing a first phase, said first phase comprising a biologically active agent, a biodegradable polymer, and a blend of at least two mutually miscible solvents for the agent and the polymer free from halogenated hydrocarbons; preparing a second phase, wherein said first phase and said second phase are substantially immiscible; preparing a quench liquid; pumping said first phase and said second phase through a static mixer into said quench liquid thereby forming microparticles containing said active agent.

In further aspects of the invention, the first phase is prepared by (1) dissolving the biologically active agent in a solution of the polymer dissolved in at least two mutually miscible solvents free from halogenated hydrocarbons, or (2) by preparing a dispersion comprising the active agent in said solvents, or (3) by preparing an emulsion comprising the active agent in said solvents.

DESCRIPTION OF THE PREFERRED EMBODIMENTS

Figure 1:
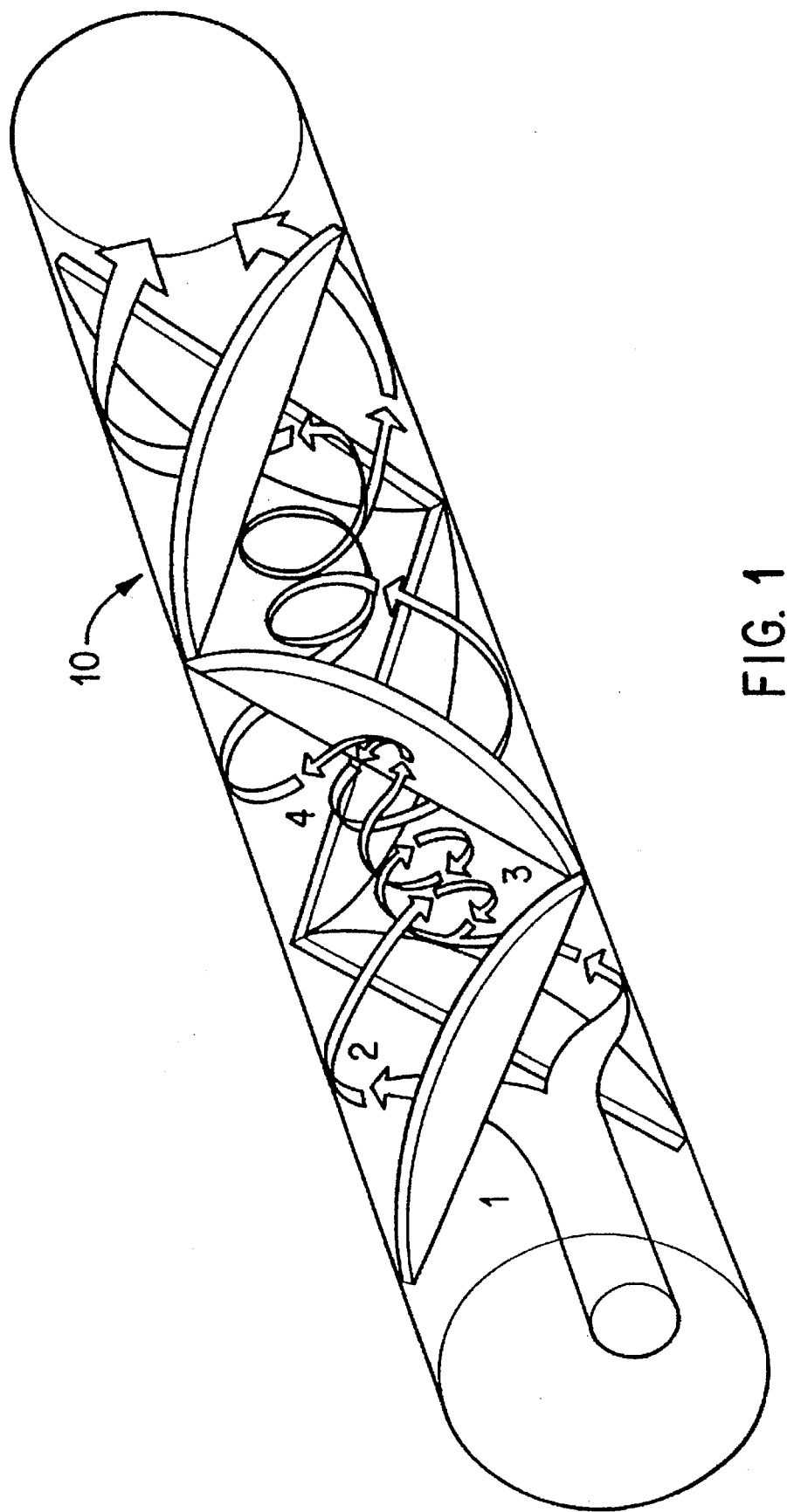
FIG. 1 illustrates flow through a static mixer.

The present invention involves the use of a solvent blend, free from halogenated hydrocarbons, comprising at least two solvents to produce biodegradable microparticles comprising at least one biologically active agent. A first solvent component of the solvent blend is a poor solvent for the active agent, but is a good solvent for the biodegradable polymer used herein. A second solvent component of the solvent blend is a good solvent for both the active agent and the polymer.

The method of the present invention provides advantages over methods known in the art. The present method provides, inter alia, a biodegradable system, an injectable system that prevents the loss of dose during treatment, the ability to mix microparticles containing different drugs, microparticles free from halogenated hydrocarbon residues, and the ability to program release (multiphasic release patterns) to give faster or slower rates of drug release as needed.

The products prepared by the method of the present invention offer the advantage of durations of action ranging from 30 to more than 200 days, depending upon the type of microparticle selected. In a preferred embodiment, the microparticles are designed to afford treatment to patients over a period of 30 to 60 days. The duration of action can be easily controlled by manipulation of the polymer composition, polymer:drug ratio, and microparticle size.

Another important advantage of the microparticles prepared by the process of the present invention is that practically all of the active agent is delivered to the patient because the polymer used in the method of the invention is biodegradable, thereby permitting all of the entrapped agent to be released into the patient.

In the process of the present invention, an active agent is dissolved or dispersed in a solvent blend free from halogenated hydrocarbons and to the agent-containing medium is added the polymeric matrix material in an amount relative to the active agent that provides a product having the desired loading of active agent. Optionally, all of the ingredients of the microparticle product can be blended in the solvent blend medium together.

The solvent system used herein is a blend of at least two solvents. These solvents must be:

(1) mutually miscible with one another, (2) capable, when blended, of dissolving or dispersing the active agent, (3) capable, when blended, of dissolving polymeric matrix material, (4) chemically inert to the active agent, (5) biocompatible, (6) substantially immiscible with the quench liquid, e.g., having a solubility of no more than about 0.1 to 25%, and (7) solvents other than halogenated hydrocarbons.

By "halogenated hydrocarbons" is meant halogenated organic solvents, i.e., $C_1$–$C_4$ halogenated alkanes, e.g., methylene chloride, chloroform, methyl chloride, carbon tetrachloride, ethylene dichloride, ethylene chloride, 2,2,2-trichloroethane, and the like.

An ideal solvent blend for encapsulation of an active agent should have a high solubility for the polymeric encapsulating agent of generally at least about 5 weight percent and, preferably, at least about 20 weight percent at 20° C. The upper limit of solubility is not critical, but if over about 50 weight percent of the solution is encapsulating polymer, the solution may become too viscous to handle effectively and conveniently. This is, of course, dependent on the nature of the encapsulating polymer and its molecular weight.

The solvent system, although substantially immiscible with the continuous phase process medium and the quenching liquid, which usually are water-based, preferably has a limited solubility therein. If the solvent system were infinitely soluble in the process medium, microdroplets would be unable to form during the emulsion phase; if the solubility of the solvent system in the extractive quenching medium is too low, however, large quantities of quenching medium are needed. Generally, solvent solubilities of from about 0.1 to about 25% in the process medium and quench medium are acceptable for use herein. It will often be advantageous for the quench medium to contain from about 70 to about 20 weight percent of the saturation point of the first solvent, i.e., the solvent of higher solubility in the quench medium, to control the rate of loss of the first solvent from the microparticles into the quench medium.

Added considerations in choosing a component of the solvent blend of the present invention include boiling point (i.e., the ease with which the solvents can be evaporated to form finished product) and specific gravity (tendency of the "oil phase" to float during emulsifying and quenching). Finally, the solvent system should have low toxicity.

Generally, the solvent blend composition will contain from about 25 to about 75 weight percent of the first solvent and, correspondingly, from about 75 to about 25 weight percent of the second solvent.

The solvent blend of the present invention is preferably a blend of at least two of the following: an ester, an alcohol, and a ketone. Preferred esters are of the structure $R^1COOR^2$ where $R^1$ and $R^2$ are independently selected from the group consisting of alkyl moieties of from 1 to 4 carbon atoms, i.e., methyl, ethyl, propyl, butyl, and isomers, thereof. The most preferred ester for use as one component of the solvent blend employed in the practice of the present invention is ethyl acetate. Preferred alcohols are of the structure $R^3CH_2OH$ where $R^3$ is selected from the group consisting of hydrogen, alkyl of from 1 to 3 carbon atoms, and aryl of from 6 to 10 carbon atoms. It is more preferred that $R^3$ be aryl. The most preferred alcohol for use as one component of the solvent blend employed in the practice of the present invention is benzyl alcohol. Preferred ketones are of the structure $R^4COR^5$ where $R^4$ is selected from the group consisting of alkyl moieties of from 1 to 4 carbon atoms, i.e., methyl, ethyl, propyl, butyl, and isomers thereof and $R^5$ is selected from the group consisting of alkyl moieties of from 2 to 4 carbon atoms, i.e., ethyl, propyl, butyl, and isomers thereof. The most preferred ketone for use as one component of the solvent blend employed in the practice of the present invention is methyl ethyl ketone.

The polymeric matrix material of the microparticles prepared by the process of the present invention is a biocompatible and biodegradable polymeric material. The term "biocompatible" is defined as a polymeric material that is not toxic to the human body, is not carcinogenic, and does not significantly induce inflammation in body tissues. The matrix material should be biodegradable in the sense that the polymeric material should degrade by bodily processes to products readily disposable by the body and should not accumulate in the body. The products of the biodegradation should also be biocompatible with the body in the same sense that the polymeric matrix is biocompatible with the body, as should any residual solvent that may remain in the microparticles.

Suitable examples of polymeric matrix materials include poly(glycolic acid), poly-D,L-lactic acid, poly-L-lactic acid, copolymers of the foregoing, poly(aliphatic carboxylic acids), copolyoxalates, polycaprolactone, polydioxonene, poly(ortho carbonates), poly(acetals), poly(lactic acid-caprolactone), polyorthoesters, poly(glycolic acid-caprolactone), polyanhydrides, polyphosphazines, and natural polymers including albumin, casein, and waxes, such as, glycerol mono- and distearate,and the like. Various commercially available poly (lactide-co-glycolide) materials (PLGA) may be used in the method of the present invention. For example, poly (d,l-lactic-co-glycolic acid) is commercially available from Medisorb Technologies International L.P. (Cincinnati, Ohio). A suitable product commercially available from Medisorb is a 50:50 poly (D,L) lactic co-glycolic acid known as MEDISORB® 5050 DL. This product has a mole percent composition of 50% lactide and 50% glycolide. Other suitable commercially available products are MEDISORB® 65:35 DL, 75:25 DL, 85:15 DL and poly(d,l-lactic acid) (d,l-PLA). Poly(lactide-co-glycolides) are also commercially available from Boehringer Ingelheim (Germany) under its Resomer mark, e.g., PLGA 50:50 (Resomer RG 502), PLGA 75:25 (Resomer RG 752) and d,l-PLA (Resomer RG 206), and from Birmingham Polymers (Birmingham, Ala.). These copolymers are available in a wide range of molecular weights and ratios of lactic acid to glycolic acid.

The most preferred polymer for use in the practice of this invention is poly(dl-lactide-co-glycolide). It is preferred that the molar ratio of lactide to glycolide in such a copolymer be in the range of from about 85:15 to about 50:50.

The molecular weight of the polymeric matrix material is of some importance. The molecular weight should be high enough to permit the formation of satisfactory polymer coatings, i.e., the polymer should be a good film former. Usually, a satisfactory molecular weight is in the range of 5,000 to 500,000 daltons, preferably about 150,000 daltons. However, since the properties of the film are also partially dependent on the particular polymeric material being used, it is very difficult to specify an appropriate molecular weight range for all polymers. The molecular weight of a polymer is also important from the point of view of its influence upon the biodegradation rate of the polymer. For a diffusional mechanism of drug release, the polymer should remain intact until all of the drug is released from the microparticles and then degrade. The drug can also be released from the microparticles as the polymeric excipient bioerodes. By an appropriate selection of polymeric materials a microparticle formulation can be made in which the resulting microparticles exhibit both diffusional release and biodegradation release properties. This is useful in affording multiphasic release patterns.

The formulation prepared by the process of the present invention contains an active agent dispersed in the microparticle polymer matrix material. The amount of agent incorporated in the microparticles usually ranges from about 1 wt. % to about 90 wt. %, preferably 30 to 50 wt. %, more preferably 35 to 40 wt. %. By weight % is meant parts of agent per total weight of microparticle. For example, 10 wt. % agent would mean 10 parts agent and 90 parts polymer by weight.

In carrying out the process of the present invention, the encapsulating polymer should be essentially 100% dissolved in the solvent blend at the time the solution is emulsified. The active agent can be dispersed or dissolved in the solvent blend at the time it, is added to the continuous phase process medium. The content of normally solid material (active agent plus encapsulating polymer) in the solvent blend at the time it is first emulsified should be at least 5 weight percent and preferably at least 20 weight percent. Minimizing solvent in the "oil phase" provides a better quality microparticle and requires less extraction medium.

One preferred active agent that can be encapsulated by the process of the present invention is norethindrone (NET)—others are risperidone and testosterone.

Ethyl acetate alone is a poor solvent for NET thereby requiring more solvent and higher temperatures than the prior art chloroform process. Although coreloads of the product microparticles are acceptable, yields, especially in the 63–90 µm range, are low. Scanning electron micrographs show these larger microparticles to be cracked open (i.e., shells) and collapsed. Higher than normal release rates for these microparticles corroborate this phenomenon.

Experiments using benzyl alcohol alone as the solvent resulted in easy control of microparticle size as determined by inspection of the quench tank contents by optical microscopy. Upon drying, however, generally poor quality was found to have resulted. Often, recovery was difficult because of stickiness. Also, solvent residuals tended to be elevated. Using a solvent system of ethyl acetate and benzyl alcohol for the "oil phase" improved the microparticle quality and release characteristics.

The mixture of ingredients in the "oil phase" solvent system is emulsified in a continuous-phase processing medium; the continuous-phase medium being such that a dispersion of microdroplets containing the indicated ingredients is formed in the continuous-phase medium.

Although not absolutely necessary, it is preferred to saturate the continuous phase process medium with at least one of the solvents forming the "oil phase" solvent system. This provides a stable emulsion, preventing transport of solvent out of the microdroplets prior to quenching. Similarly, a vacuum may be applied as in U.S. Pat. No. 4,389,330. Where ethyl acetate and benzyl alcohol are the components of the solvent system, the aqueous phase of the emulsion preferably, contains 1 to 8 weight percent ethyl acetate and 1 to 4 weight percent benzyl alcohol.

Usually, a surfactant or a hydrophilic colloid is added to the continuous-phase processing medium to prevent the solvent microdroplets from agglomerating and to control the size of the solvent microdroplets in the emulsion. Examples of compounds that can be used as surfactants or hydrophilic colloids include, but are not limited to, poly(vinyl alcohol), carboxymethyl cellulose, gelatin, poly(vinyl pyrrolidone), Tween 80, Tween 20, and the like. The concentration of surfactant or hydrophilic colloid in the process medium should be sufficient to stabilize the emulsion and will affect the final size of the microparticles. Generally the concentration of the surfactant or hydrophilic colloid in the process medium will be from about 0.1% to about 10% by weight based on the process medium, depending upon the surfactant or hydrophilic colloid, the "oil phase" solvent system, and the processing medium used. A preferred dispersing medium combination is a 0.1 to 10 wt. %, more preferably 0.5 to 2 wt. %, solution of poly(vinyl alcohol) in water.

The emulsion can be formed by mechanical agitation of the mixed phases or by adding small drops of the organic phase that contains active agent and wall forming material to the continuous phase processing medium. The temperature during the formation of the emulsion is not especially critical, but can influence the size and quality of the microparticles and the solubility of the active agent in the continuous phase. Of course, it is desirable to have as little of the active agent in the continuous phase as possible. Moreover, depending on the solvent blend and continuous-phase processing medium employed, the temperature must not be too low or the solvent and processing medium may solidify or become too viscous for practical purposes. On the other hand, it must not be so high that the processing medium will evaporate or that the liquid processing medium liquid processing medium will not be maintained. Moreover, the temperature of the emulsion cannot be so high that the stability of the particular active agent being incorporated in the microparticles is adversely affected. Accordingly, the dispersion process can be conducted at any temperature that maintains stable operating conditions, preferably from about 20° C. to about 60° C., depending upon the active agent and excipient selected.

As stated above, in order to create microparticles containing an active agent, an organic phase and an aqueous phase are combined. The organic and aqueous phases are largely or substantially immiscible, with the aqueous phase constituting the continuous phase of the emulsion. The organic phase includes the active agent as well as the wall forming polymer, i.e., the polymeric matrix material. The organic phase is prepared by dissolving or dispersing the active agent(s) in the organic solvent system of the present invention. The organic phase and the aqueous phase are combined under the influence of mixing means.

A preferred type of mixing means is a static mixer and a preferred method of encapsulating the active agent to form the controlled release microparticles of the present invention involves the use of such a static mixer. Preferably the combined organic and aqueous phases are pumped through a static mixer to form an emulsion and into a large volume of quench liquid, to obtain microparticles containing the active agent encapsulated in the polymeric matrix material.

In many of the known techniques for the microencapsulation of biological or pharmaceutical agents, the microparticles form when the solvent containing the active agent and the polymer is emulsified or dispersed in an immiscible second solvent by stirring, agitating, vibrating, or some other dynamic mixing technique, often for a relatively long period of time. Such dynamic mixing techniques have several drawbacks. For example, it is difficult to control the size of the resulting microparticles or the distribution of sizes obtained. As a consequence, use of dynamic mixing also presents problems when preparing microparticles containing biological or pharmaceutical agents on a production or commercial scale. Particularly, production equipment includes a costly emulsion tank, including equipment to stir or agitate the fluids. One of the controlling factors for overall process time is the time required to form a uniform emulsion. Increased batch sizes in larger tanks require a longer time to form the emulsion, resulting in a longer overall production process time. Longer exposure times of the active agent to process solvents and polymers in solution can lead to degradation or deactivation of the active agent. Scale-up to a production process from a laboratory emulsion process is particularly difficult for microencapsulation of biological or pharmaceutical agents since, as the batch and tank size are increased, stir speeds and viscosities within the larger tank have to be empirically determined, and optimized, by trial and error at each stage of the scale-up. This process is not only time consuming, but imprecise.

Accordingly, one advantage of preparing microparticles using a static mixer is that accurate and reliable scaling from laboratory to commercial batch sizes can be done while achieving a narrow and well defined size distribution of microparticles containing biologically or pharmaceutically active agents. A further advantage of this method is that the same equipment can be used to form microparticles containing active agents of a well defined size distribution for varying batch sizes. Yet another advantage of the method is that high quality microparticles having a high concentration of active agent can be obtained using a single step to remove solvent without the need for a two-step solvent removal process as described in the above-mentioned Tice et al. patent (U.S. Pat. No. 4,389,330). In addition to improving process technology, static mixers are low maintenance, their small size requires less space than dynamic mixers, they have low energy demands, and comparatively low investment costs.

Static or motionless mixers consist of a conduit or tube in which is received a number of static mixing elements. Static mixers provide uniform mixing in a relatively short length of conduit, and in a relatively short period of time. With static mixers, the fluid moves through the mixer, rather than some part of the mixer, such as a blade, moving through the fluid.

Flow through one type of static mixer is illustrated in FIG. 1. A pump (not shown) introduces a stream of one or more fluids into a static mixer 10 as shown generally at 1. The stream is split and forced to opposite outside walls as shown generally at 2. A vortex is created axial to the centerline of static mixer 10, as shown generally at 3. The vortex is sheared and the process recurs, but with the opposite rotation, as shown generally at 4. The clockwise/counter-clockwise motion ensures a homogeneous product.

Figure 2:
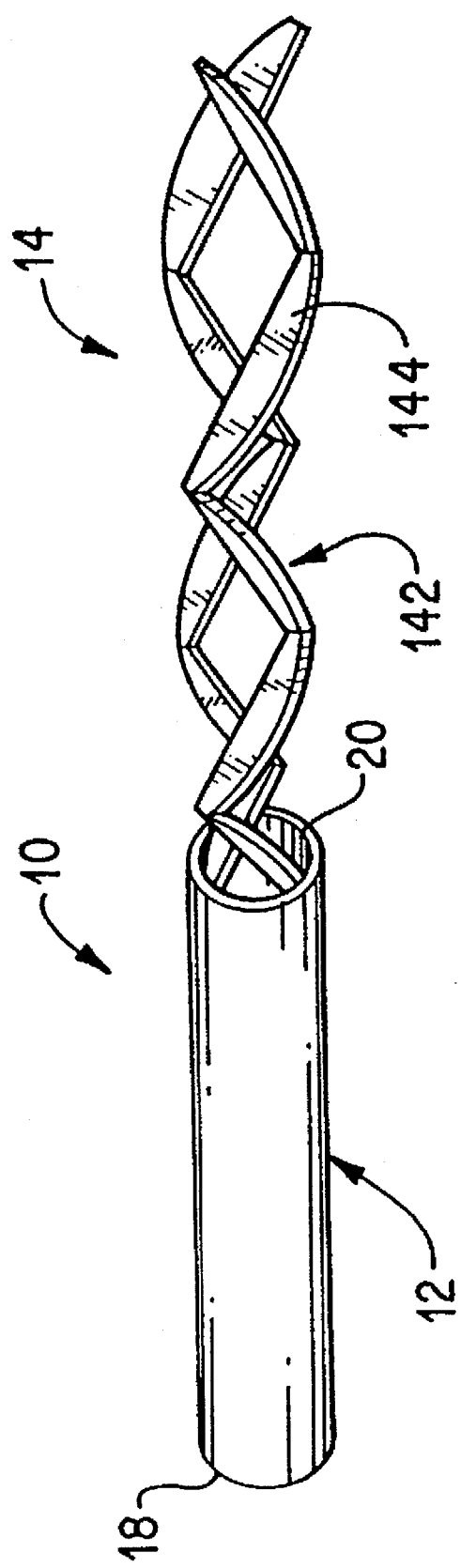
FIG. 2 shows a static mixer which may be used in the process of the present invention.

One example of a static mixer is shown in FIG. 2. Static mixer 10 includes a number of stationary or static mixing elements 14 arranged in a series within a conduit or pipe 12. The number of elements can range from 4 to 32 or more. Conduit 12 is circular in cross-section and open at opposite ends 18 and 20 for introducing and withdrawing fluids. Mixing element 14 comprises segments 142. Each segment 142 consists of a plurality of generally flat plates or vanes 144. The two substantially identical segments 142 are preferably axially staggered with respect to each other. A static mixer as shown in FIG. 2 is more fully described in U.S. Pat. No. 4,511,258 which is incorporated herein by reference.

When using a static mixer to form an emulsion, a variety of factors determine emulsion droplet size. These factors include the density and viscosity of the various solutions or phases to be mixed, volume ratio of the phases, interfacial tension between the phases, static mixer parameters (conduit diameter; length of mixing element; number of mixing elements), and fluid velocity through the static mixer. Temperature is a variable because it affects density, viscosity, and interfacial tension. The primary controlling variable is fluid velocity. Shear rate and pressure drop per unit length of static mixer are also important parameters. Particularly, droplet size decreases as fluid velocity increases and alternatively, droplet size increases as fluid velocity (and pressure drop) decreases. Droplets will reach an equilibrium size after moving through a fixed number of elements for a given flow rate. The higher the flow rate, the fewer elements needed. Because of these relationships, scaling from laboratory batch sizes to commercial batch sizes is reliable and accurate, and the same equipment can be used for laboratory and commercial batch sizes.

In a process of the present invention, the organic phase and the aqueous phase are pumped so that the two phases flow simultaneously through a static mixer, thereby forming an emulsion which comprises microparticles containing the active agent encapsulated in the polymeric matrix material. The organic and aqueous phases are pumped through the static mixer into a large volume of quench liquid. The quench liquid may be plain water, a water solution, or other suitable liquid. Organic solvent may be removed from the microparticles while they are washing or being stirred in the quench liquid. The process of the present invention, whereby organic and aqueous phases are pumped through a static mixer into a quench liquid for solvent removal, results in the formation of high quality microparticles having a high concentration of active agent without the need for the two-step solvent removal process described in the above-mentioned Tice et al. U.S. Pat. No. 4,389,330. After the microparticles are washed in a quench liquid to extract or remove the organic solvent, they are isolated, as through a sieve, and dried.

In another process of the present invention, the organic phase is comprised of a polymer solution and an active agent which may be suspended as a dry powder or dissolved in an aqueous solution and emulsified. The polymer is dissolved in an appropriate organic solvent, preferably a non-halogenated solvent such as ethyl acetate. The organic phase is combined with a non-solvent in a static mixer where coacervation or precipitation of the polymer droplets around the active agent particles or droplets, i.e., phase separation, takes place. The residence time of the solvent and non-solvent flowing through the static mixer is an important factor in the process. The residence time can be altered by changing the dimensions of the mixing elements and conduit as well as the linear velocities of the solutions flowing through the static mixer. Other important factors that may affect the formation of microspheres are the density and viscosity of the two phases to be mixed, the volume ratio of the phases, and the interfacial tension between the phases. The size control of the microspheres, however, is determined primarily by the size and uniformity of the initial suspension or emulsion of the active agent in the organic phase.

Figure 3:
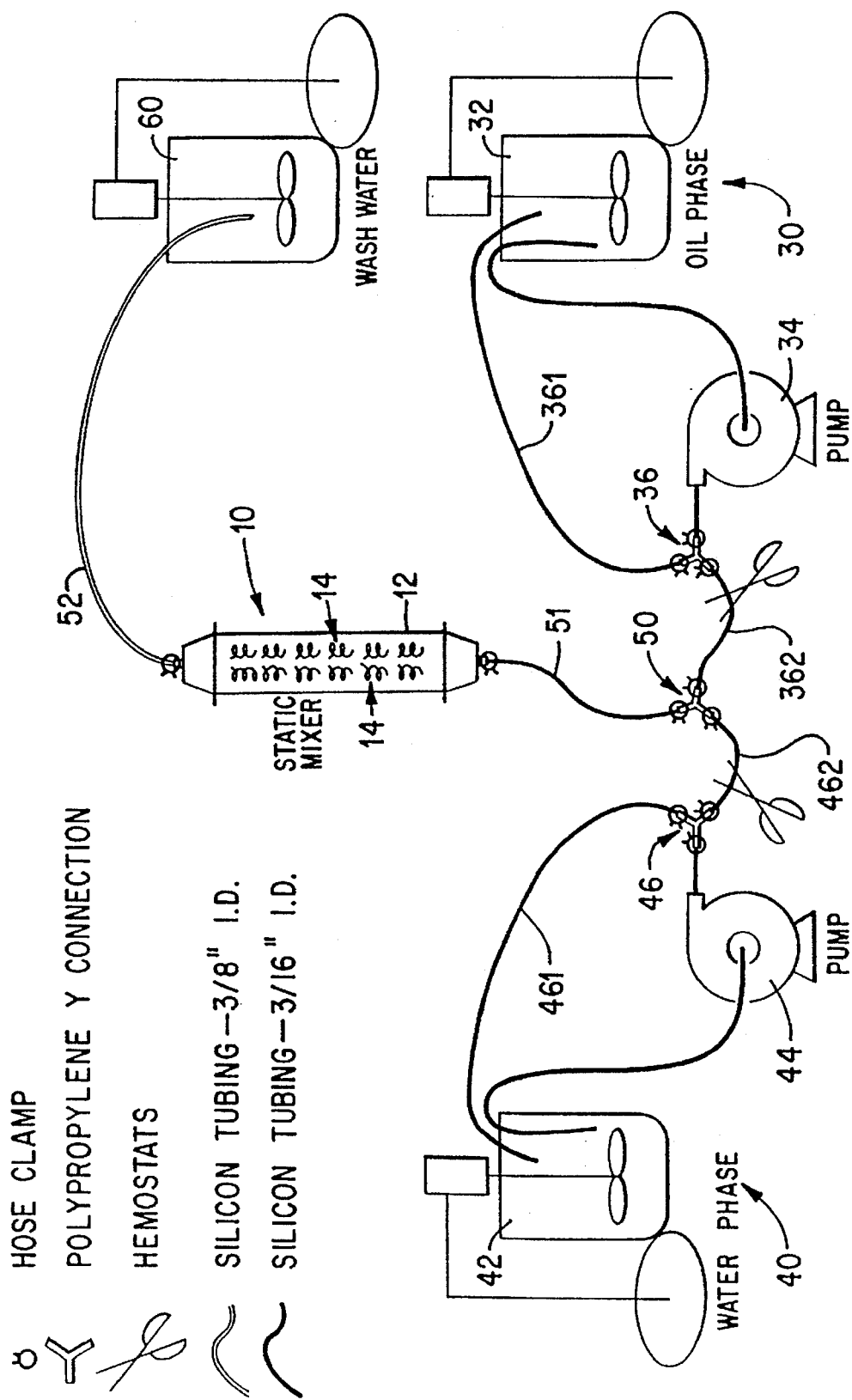
FIG. 3 shows a laboratory set-up for carrying out a preferred process for preparing the microparticles of the present invention.

A laboratory set up for carrying out a static mixer process is illustrated in FIG. 3. An organic or oil phase 30 is prepared by dissolving an active agent and a polymeric matrix material in a stirred pot 32. However, the process is not limited to preparing organic phase 30 by dissolving an active agent. Alternatively, organic phase 30 may be prepared by dispersing an active agent in a solution containing a polymeric matrix material. In such a dispersion, the active agent is only slightly soluble in organic phase 30. Alternatively, organic phase 30 may be prepared by preparing an emulsion containing an active agent and a polymeric matrix material (double emulsion process). In the double emulsion process, a primary emulsion is prepared that contains an active agent and a polymeric matrix material (organic phase 30). The primary emulsion may be a water-in-oil emulsion, an oil-in-water emulsion, or any suitable emulsion. The primary emulsion (organic phase 30) and an aqueous phase are then pumped through a static mixer to form a second emulsion that comprises microdroplets containing the active agent encapsulated in the polymeric matrix material. An example of preparing microparticles containing an active agent using the double emulsion process of the present invention is provided below as Example 8.

Organic phase 30 is pumped out of stirred pot 32 by a magnetically driven gear pump 34. However, it is understood that any suitable pumping means may be used. The discharge of pump 34 feeds a "Y" connection 36. One branch 361 of "Y" connection 36 returns to pot 32 for recirculation flow. The other branch 362 feeds into an in-line static mixer 10. Aqueous or water phase 40 is prepared in like manner, with a stirred pot 42, a magnetically driven gear pump 44, and a "Y" connection 46. One branch 461 of "Y" connection 46 returns to pot 42 for recirculation flow. The other branch 462 feeds into in-line static mixer 10.

Branches 362 and 462 from each solution, which feed in-line static mixer 10, are joined by another "Y" connection 50 and feed through mixer inlet line 51 into static mixer 10. Static mixer 10 discharges through mixer outlet line 52 into wash tank 60. Silicone tubing and polypropylene fittings are used in the system illustrated in FIG. 3. Silicone tubing having ⅜ inch ID is used for all lines except mixer outlet line 52. Smaller diameter tubing (3/16 inch ID) is used for mixer outlet line 52 to prevent collapse of the emulsion both in mixer outlet line 52 and upon entering wash tank 60.

In one embodiment of the process, pumps 34 and 44 are started in recirculation mode and desired flow rates are set for organic phase 30 and water phase 40. The flow rate of water phase 40 is preferably greater than the flow rate of organic phase 30. However, the two flow rates may be substantially the same. The ratio of the flow rate of water phase 40 to the flow rate of organic phase 30 is preferably in the range of 1:1 to 10:1. "Y" connection 46 is then switched so that water phase 40 flows through branch 462 to static mixer 10. Once water phase 40 fills mixer inlet line 51, static mixer 10, and mixer outlet line 52; "Y" connection 36 is switched so that organic phase 30 flows through branch 362 to static mixer 10. Organic phase 30 and aqueous phase 40 at this point flow simultaneously through static mixer 10. When the desired amount of organic phase has been pumped to static mixer 10, "Y" connection 36 is switched to recirculation through branch 361. Water phase 40 continues to flow for a short time to clean out any organic phase remaining in mixer inlet line 51, static mixer 10, and mixer outlet line 52. "Y" connection 46 is then switched to recirculation through branch 461.

Organic phase 30 and aqueous phase 40 are mixed in static mixer 10 to form an emulsion. The emulsion formed comprises microdroplets containing active agent encapsulated in a polymeric matrix material. The microdroplets are stirred in wash tank 60 which contains a quench solution in order to remove the organic solvent from the microdroplets resulting in the formation of hardened microparticles. The microparticles are then isolated from the aqueous quench solution by any convenient means of separation; the fluid can be decanted from the microparticles or the microparticle suspension can be filtered or a sieve column can be used. Various other combinations of separation techniques can be used, if desired. The microparticles are then dried using conventional drying techniques, and further size isolation may be carried out.

Following the movement of the microdroplets from the static mixer and entrance into the wash tank, the continuous-phase processing medium is diluted and the remainder of the solvent in the microparticles is removed by extraction. In this extractive quench step, the microparticles can be suspended in the same continuous-phase processing medium used during emulsification, with or without hydrophilic colloid or surfactant, or in another liquid. The extraction medium removes the solvent from the microparticles, but does not dissolve them. During the extraction, the extraction medium containing dissolve solvent can, optionally, be removed and replaced with fresh extraction medium. This is best done on a continual or continuous basis where the rate of extraction medium replenishment is critical. If the rate is too slow, active agent crystals may protrude from the microparticles or grow in the extraction medium. This critical rate of extraction medium replenishment for a given process is a variable that can be determined at the time the process is performed and, therefore, no precise limits for the rate need be predetermined. After the remainder of the solvent has been removed, the microparticles are isolated as stated above and are then dried by exposure to air or by other conventional drying techniques, such as, vacuum drying, drying over a desiccant, or the like. This process is very efficient in encapsulating an active agent since core loadings of up to about 80 wt. %, preferably up to about 50 wt. % can be obtained.

One of the solvents in the blend of solvents used to form the "oil phase" droplets in the emulsion will be extracted more quickly than the other solvent., e.g., the first solvent, ethyl acetate, in the case of the preferred ethyl acetate/benzyl alcohol blend. Thus, high residuals of the second solvent (here, benzyl alcohol) are left behind. Owing to the high boiling point of benzyl alcohol, it is not easily removed by exposure of the microparticles to air or other conventional evaporative means. To overcome this, some of the more rapidly extracted solvent is added to the extraction medium prior to addition of the emulsion. The concentration of the more rapidly extracted solvent in the extraction medium generally is from about 20 to about 70% of the saturation point of the solvent in the medium at the temperature to be used for the extraction. Thus, when the emulsion is added to the quench liquid, extraction of the more rapidly extracted solvent is retarded and more of the second, more slowly extracted, solvent is removed.

The exact amount of this more-rapidly-extracted solvent "spike" is of importance to final microparticle quality. Too much solvent (i.e., near the saturation point) results in porous microparticles with additive agent visible on the surface, causing what may be an undesirable high rate of release. Too little solvent in the extraction medium results in high residuals of the more slowly extracted solvent and poor microparticle quality. The temperature of the extraction medium is also important as it affects solvent solubility and rate of extraction.

Both temperature and amount of solvent spike may be adjusted to provide the final desired product characteristics, i.e., highly porous, quick releasing microparticles or slow releasing microparticles having a low porosity.

The quench liquid may be plain water, a water solution, or other suitable liquid, the volume, amount, and type of which depends on the solvents used in the emulsion phase. The quench liquid preferably is water. Generally, the quench liquid volume is on the order of 10 times the saturated volume (i.e., 10 times the quench volume needed to absorb completely the volume of solvent in the emulsion). Depending on the solvent system, however, quench volume can vary from about 2 to about 20 times the saturated volume. Additionally, it is convenient to describe the quench volume requirement relative to batch size (microparticle product). This ratio is an indication of efficiency of the extraction step and, in some cases, dictates the batch size for a given set of equipment. The larger the ratio, the more volume is required per product weight. On the other hand, with a smaller ratio, more product may be obtained from the same amount of quench volume. This ratio may vary from about 0.1 to about 10 liters of quench volume per gram of microparticles produced. Processes with a ratio of less than about 1 liter per gram are preferred.

When using the preferred solvent combination of benzyl alcohol and ethyl acetate, the ethyl acetate of the quench liquid appears to affect the residual solvent level in the product microparticles. At low ethyl acetate contents in the quench liquid, the benzyl alcohol residuals in the microparticles are high while ethyl acetate may be almost non-detectable. At high ethyl acetate contents in the quench liquid, 5–7% by weight or more, more ethyl acetate may be retained by the microparticles than benzyl alcohol. At a quench volume of about 1 liter per gram of active agent and polymeric encapsulating material being quenched, about 3–4 weight percent ethyl acetate in the quench liquid is optimal at 0°–4° C. The coreload of the microparticles varies slightly with changes in ethyl acetate concentration in the quench liquid, decreasing with high and low concentrations of ethyl acetate. In vitro release rates from the microparticles vary substantially as the ethyl acetate content of the quench liquid is varied. In the case of NET, quicker release of NET is observed at the extreme ethyl acetate contents. Observation with a scanning electron microscope shows the presence of NET and pores on the microparticle surface when extremes of ethyl acetate are present in the quench liquid.

Altering the volume of the quench liquid also has a profound effect on the relative amount of solvent residuals in the microparticles. At low volumes, the ratio of benzyl alcohol to ethyl acetate is high and decreases to less than one as quench volume is increased to about 1.5 L per gram of active agent and polymeric encapsulating material being quenched. The rate of active agent release from the product microparticles is markedly high. (At 0.125 L quench liquid per gram of solution of NET and polymeric encapsulating material, scanning electron micrographs show that the product microparticles are extremely porous. From 0.25 to 1.5 L quench liquid per gram of solution of NET and polymeric encapsulating material, the NET release rate from the product microparticles varies slightly with a possible minimum at 1 L quench liquid per gram of NET and polymeric encapsulating material being quenched.)

The process of the present invention whereby microparticles are prepared using a static mixer can be carried out for a variety of techniques used to encapsulate active agents. The process of the present invention is not limited to the solvent extraction technique discussed above, but can be used with other encapsulation techniques. For example, the process of the present invention can also be used with a phase separation encapsulation technique. To do so, an organic phase is prepared that comprises an active agent suspended or dispersed in a polymer solution. The non-solvent second phase is free from solvents for the polymer and active agent. A preferred non-solvent second phase is silicone oil. The organic phase and the non-solvent phase are pumped through a static mixer into a non-solvent quench liquid, such as heptane. The semi-solid particles are quenched for complete hardening and washing. Examples of using such a process are provided below as Examples 11–14.

The microparticle product is usually made up of particles of a spherical shape, although sometimes the microparticles may be irregularly shaped. The microparticles can vary in size, ranging from submicron to millimeter diameters. Preferably, microparticles of 1–500 microns, more preferably, 25–180 microns, are prepared, whereby administration of the microparticles to a patient can be carried out with a standard gauge needle.

Preferably, the drug loaded microparticles are dispensed to patients in a single administration, releasing the drug in a constant or pulsed manner into the patient and eliminating the need for repetitive injections.

The active agent bearing microparticles are obtained and stored as a dry material. Prior to administration to a patient, the dry microparticles can be suspended in an acceptable pharmaceutical liquid vehicle, such as, a 2.5 wt. % solution of carboxymethyl cellulose, whereupon the suspension of microparticles is injected into the body.

The microparticles can be mixed by size or by type so as to provide for the delivery of active agent to the patient in a multiphasic manner and/or in a manner that provides different active agents to the patient at different times, or a mixture of active agents at the same time. For example, secondary antibiotics, vaccines, or any desired active agent, either in microparticle form or in conventional, unencapsulated form can be blended with a primary active agent and provided to the patient.

Suitable active agents include estrogens such as diethyl stilbestrol, 17-beta-estradiol, estrone, ethinyl estradiol, mestranol, and the like; progestins such as norethindrone, norgestryl, ethynodiol diacetate, lynestrenol, medroxyprogesterone acetate, dimesthisterone, megestrol acetate, chlormadinone acetate, norgestimate, norethisterone, ethisterone, melengestrol, norethynodrel and the like; and spermicidal compounds such as nonylphenoxypolyoxyethylene glycol, benzethonium chloride, chlorindanol and the like.

Other biologically active agents that can be incorporated using the process of the present invention include gastrointestinal therapeutic agents such as aluminum hydroxide, calcium carbonate, magnesium carbonate, sodium carbonate and the like; non-steroidal antifertility agents; parasympathomimetic agents; psychotherapeutic agents; risperidone; major tranquilizers such as chlorprommazine HCl, clozapine, mesoridazine, metiapine, reserpine, thioridazine and the like; minor tranquilizers such as chlordiazepoxide, diazepam, meprobamate, temazepam and the like; rhinological decongestants; sedative-hypnotics such as codeine, phenobarbital, sodium pentobarbital, sodium secobarbital and the like; steroids such as testosterone and testosterone propiohate; sulfonamides; sympathomimetic agents; vaccines; vitamins and nutrients such as the essential amino acids; essential fats and the like; antimalarials such as 4-aminoquinolines, 8-aminoquinolines, pyrimethamine and the like, anti-migraine agents such as mazindol, phentermine and the like; anti-Parkinson agents such as L-dopa; antispasmodics such as atropine, methscopolamine bromide and the like; antispasmodics and anticholinergic agents such as bile therapy, digestants, enzymes and the like; antitussives such as dextromethorphan, noscapine and the like; bronchodilators; cardiovascular agents such as anti-hypertensive compounds, Rauwolfia alkaloids, coronary vasodilators, nitroglycerin, organic nitrates, pentaerythritotetranitrate and the like; electrolyte replacements such as potassium chloride; ergotalkaloids such as ergotamine with and without caffeine, hydrogenated ergot alkaloids, dihydroergocristine methanesulfate, dihydroergocornine methanesulfonate, dihydroergokroyptine methanesulfate and combinations thereof; alkaloids such as atropine sulfate, Belladonna, hyoscine hydrobromide and the like; analgetics; narcotics such as codeine, dihydrocodienone, meperidine, morphine and the like; non-narcotics such as salicylates, aspirin, acetaminophen, d-propoxyphene and the like; antibiotics such as the cephalosporins, chloranphenical, gentamicin, Kanamycin A, Kanamycin B, the penicillins, ampicillin, streptomycin A, antimycin A, chloropamtheniol, metromidazole, oxytetracycline penicillin G, the tetracyclines, and the like; anti-cancer agents; anticonvulsants such as mephenytoin, phenobarbital, trimethadione; anti-emetics such as thiethylperazine; antihistamines such as chlorophinazine, dimenhydrinate, diphenhydramine, perphenazine, tripelennamine and the like; anti-inflammatory agents such as hormonal agents, hydrocortisone, prednisolone, prednisone, non-hormonal agents, allopurinol, aspirin, indomethacin, phenylbutazone and the like; prostaglandins; cytotoxic drugs such as thiotepa, chlorambucil, cyclophosphamide, melphalan, nitrogen mustard, methotrexate and the like; antigens of such microorganisms as *Neisseria gonorrhea, Mycobacterium tuberculosis,* Herpes virus (humonis, types 1 and 2), *Candida albicans, Candida tropicalis, Trichomonas vaginalis, Haemophilus vaginalis,* Group B *Streptococcus ecoli, Microplasma hominis, Hemophilus ducreyi, Granuloma inguinale, Lymphopathia venereum, Treponema pallidum, Brucella abortus, Brucella melitensis, Brucella suis, Brucella canis, Campylobacter fetus, Campylobacter fetus intestinalis, Leptospira pomona, Listeria monocytogenes, Brucella ovis,* Equine herpes virus 1, Equine arteritis virus, IBR-IBP virus, BVD-MB virus, *Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Babesia caballi, Clostridium tetani,* and the like; antibodies that counteract the above microorganisms; and enzymes such as ribonuclease, neuramidinase, trypsin, glycogen phosphorylase, sperm lactic dehydrogenase, sperm hyaluronidase, adenosinetriphosphatase, alkaline phosphatase, alkaline phosphatase esterase, amino peptidase, trypsin, chymotrypsin, amylase, muramidase, acrosomal proteinase, diesterase, glutamic acid dehydrogenase, succinic acid dehydrogenase, beta-glycophosphatase, lipase, ATP-ase alpha-peptate gamma-glutamylotranspeptidase, sterol-3-beta-ol-dehydrogenase, and DPN-di-aprorase.

Still other macromolecular bioactive agents that may be chosen for incorporation include, but are not limited to, blood clotting factors, hemopoietic factors, cytokines, interleukins, colony stimulating factors, growth factors, and analogs and fragments thereof.

The following examples further describe the materials and methods used in carrying out the invention. The examples are not intended to limit the invention in any manner.

EXAMPLE 1

Preparation of 30%, 33%, and 50% Theoretically Loaded Norethindrone Microparticles A 1 kg batch of 30% norethindrone loaded microparticles is prepared using a ¾" diameter×12 element static mixer (Koflo, M/N: ¾-TU-3-12RH-11, Koflo Corp., Cary, Ill.). The polymer/drug solution (organic phase) is prepared as follows. 329 gm norethindrone USP is dissolved in a heated (65°–70° C.) solution of 770 gm Medisorb® 85:15 dl PLGA (Inherent Viscosity (IV)=0.65 dl/gm) in 2.2 kg ethyl acetate NF and 2.2 kg benzyl alcohol NF. The solution is filtered (0.2 μm) and maintained at 65°–70° C. The process water solution (aqueous phase) is prepared as follows. 150 gm of poly(vinyl alcohol) (PVA—Du Pont Elvanol® 51-05) is added to 27.27 kg of WFI (Water For Injection) and heated (65°–70° C.) until dissolved, and then filtered (0.2 μm). To this solution, 810 gm of filtered (0.2 μm) benzyl alcohol and 1770 gm of filtered (0.2 μm) ethyl acetate are added. The solution is maintained at 65°–70° C. The quench solution is prepared as follows: 26.25 kg of ethyl acetate NF (0.2 μm filtered) is dissolved in 750 liters of cold WFI and maintained at 2°–4° C.

The organic phase is pumped through the static mixer at a flow rate of 909 cc/min, and the aqueous phase at a flow rate of 4500 cc/min into the quench solution. After 1 hour of quench, the material is passed through 90 and 25 μm screens. The 25–90 μm portion is vacuum dried with agitation for 36 hours at ambient temperature. The process yield is 650 gm of norethindrone loaded microparticles.

A 1 kg batch of 33% norethindrone loaded microparticles is prepared using a ¾" diameter×12 element static mixer (Koflo, M/N: ¾-TU-3-12RH-11, Koflo Corp., Cary, Ill.). The polymer/drug solution (organic phase) is prepared as follows. 363 gm norethindrone USP is dissolved in a heated (65°–70° C.) solution of 737 gm MEDISORB® 85:15 dl PLGA (IV=0.62 dl/gm) in 2.2 kg ethyl acetate NF and 2.2 kg benzyl alcohol NF. The solution is filtered (0.2 μm) and maintained at 65°–70° C. The process water solution (aqueous phase) is prepared as follows. 150 gm of PVA (Du Pont Elvanol® 51-05) is added to 27.27 kg of WFI and heated (65°–70° C.) until dissolved, and then filtered (0.2 μm). To this solution, 810 gm of filtered (0.2 μm) benzyl alcohol and 1770 gm of filtered (0.2 μm) ethyl acetate are added. The solution is maintained at 65°–70° C. The quench liquid is prepared as follows. 750 liters of 3.5% ethyl acetate NF (0.2 μm filtered) is dissolved in WFI and maintained at 2°–4° C.

The organic phase is pumped through the static mixer at a flow rate of 909 cc/min, and the aqueous phase at a flow rate of 4500 cc/min into the quench liquid. After 1 hour of quench, the material is passed through 90 and 25 μm screens. The 25–90 μm portion is vacuum dried with agitation for 36 hours at ambient temperature. The process yield is 630 gm of norethindrone loaded microparticles.

A 1 kg batch of 50% norethindrone loaded microparticles is prepared using a ¾" diameter×12 element static mixer (Koflo, M/N: ¾-TU-3-12RH-11, Koflo Corp., Cary, Ill.). The polymer/drug solution (organic phase) is prepared as follows. 546 gm norethindrone USP is dissolved in a heated (65°–70° C.) solution of 550 gm MEDISORB® 85:15 dl PLGA (a copolymer of 85 mole % lactic acid and 15 mole % glycolic acid, poly(lactide-co-glycolide)) (IV=0.62 dl/gm) in 2.2 kg ethyl acetate NF and 2.2 kg benzyl alcohol NF. The solution is filtered (0.2 μm) and maintained at 65°–70° C. The process water solution (aqueous phase) is prepared as follows. 150 gm of PVA (Du Pont Elvanol® 51-05) is added to 27.27 kg of WFI and heated (65°–70° C.) until dissolved, and then filtered (0.2 μm). To this solution, 810 gm of filtered (0.2 μm) benzyl alcohol and 1770 gm of filtered (0.2 μm) ethyl acetate are added. The solution is maintained at 65°–70° C. The quench solution is prepared as follows: 26.25 kg of ethyl acetate NF (0.2 μm filtered) is dissolved in 750 liters of cold WFI and maintained at 2°–4° C.

The organic phase is pumped through the static mixer at a flow rate of 909 cc/min, and the aqueous phase at a flow rate of 4500 cc/min into the quench solution. After 1 hour of quench, the material is passed through 90 and 25 μm screens. The 25–90 μm portion is vacuum dried with agitation for 36 hours at ambient temperature. The process yield is 685 gm of norethindrone loaded microparticles.

Figure 4:
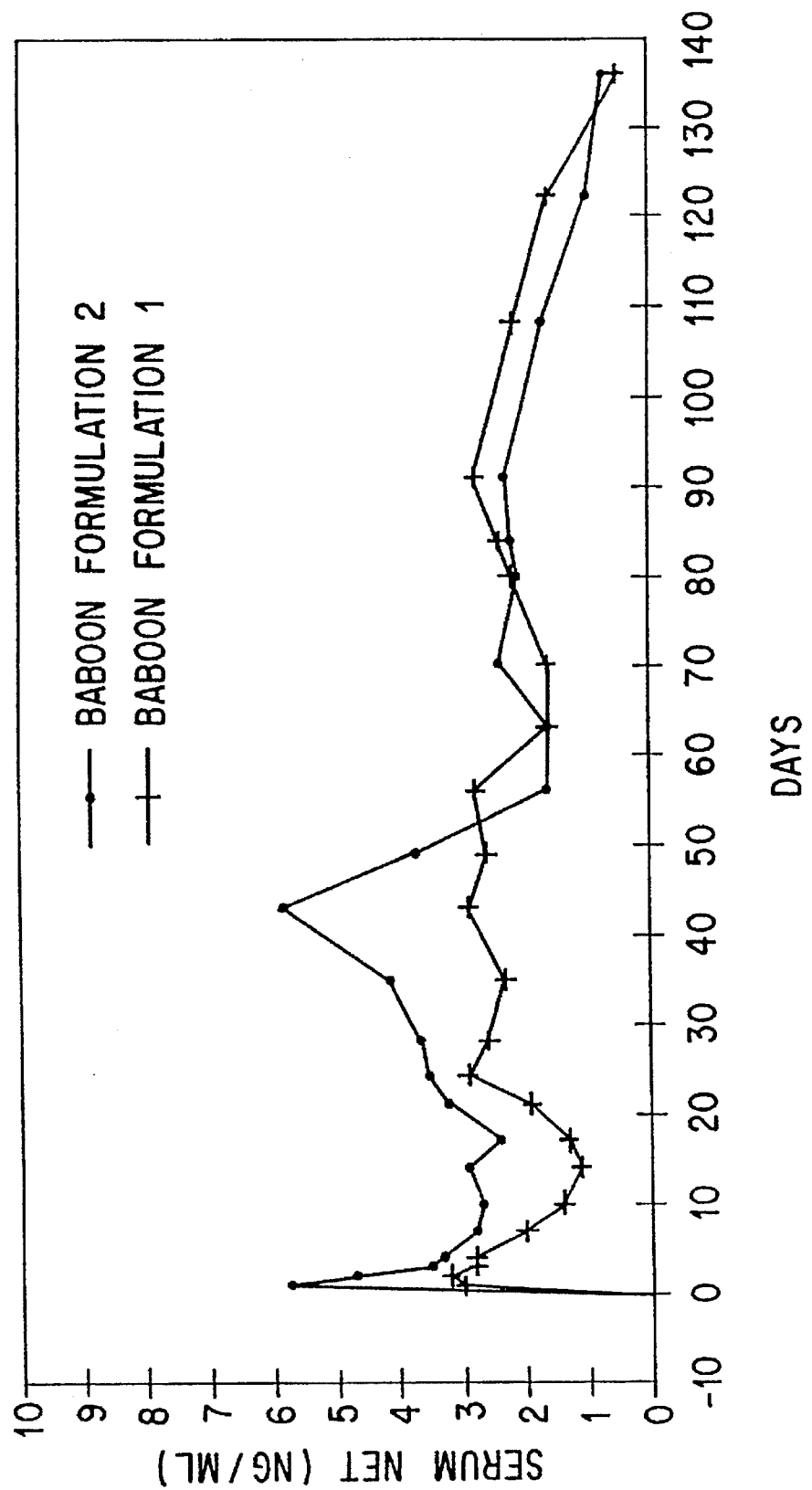
FIG. 4 depicts a graph of time release animal test data for two formulations of norethindrone loaded microparticles.

The 30% and 50% loaded particles were then used to prepare two 65 mg (NET) formulations for injecting into baboons. Baboon Formulation 1 consisted of 35% of the 50% loaded particles and 65% of the 30% loaded particles. Baboon Formulation 2 consisted of 50% of each of the 30% loaded and 50% loaded particles. Time release data for Baboon Formulations 1 and 2 are shown in FIG. 4.

EXAMPLE 2

Preparation of 35% Theoretically Loaded Risperidone Microparticles (Batch Prodex 2)

First, the aqueous phase (solution A) is prepared by weighing and mixing 906.1 g 1% poly(vinyl alcohol) (Vinol 205, Air Products and Chemical Inc., Allentown, Pa.), 29.7 g benzyl alcohol (J. T. Baker, Phillipsburg, N.J.) and 65.3 g ethyl acetate (Fisher Scientific, Fair Lawn, N.J.). Then the organic phase (solution B) is prepared by dissolving 29.3 g of high viscosity 75:25 dl (polylactide-co-glycolide), (Medisorb Technologies International, L.P., Cincinnati, Ohio) in 108.7 g ethyl acetate and 108.4 g benzyl alcohol. Once the polymer is completely dissolved, 15.7 g risperidone base (Janssen Pharmaceutica, Beerse, Belgium) is added and dissolved in the polymer solution. The exposure time of the dissolved risperidone with the polymer is kept to a minimum (<10 minutes). Solutions A and B are then pumped through a ¼ inch diameter static mixer (Cole Parmer L04667-14) via a gear drive pump and head (Cole-Parmer L07149-04, L07002-16) at flow rates of 198 and 24 mL/minute, respectively, into a quench medium (wash) composed of 55 liters of water for injection containing 1,276.0 g of ethyl acetate, 92.3 g (0.02 Molar) of anhydrous sodium bicarbonate, and 116.2 g (0.02 Molar) of anhydrous sodium carbonate (Mallinckrodt Specialty Chemicals, Paris, Ky.) at 11° C. The microparticles are allowed to stir in this first wash for 1 and ¾ hours, then isolated by sieving with a 25 micron sieve. The product retained by the sieve is transferred to a second 20-liter wash of WFI at 13° C. After stirring in the second wash for 2 and ¼ hours, the microparticles are isolated and size fractionated by sieving through a stainless-steel sieve column composed of 25 and 180 micron mesh sizes. The microparticles are dried overnight, then collected and weighed.

EXAMPLE 3

Preparation of 40% Theoretically Loaded Risperidone Microparticles (Batch Prodex 3)

First, the aqueous phase (solution A) is prepared by weighing and mixing 904.4 g 1 % poly(vinyl alcohol), (Vinol 205, Air Products and Chemical Inc., Allentown, Pa.), 30.1 g benzyl alcohol (J. T. Baker, Phillipsburg, N.J.), and 65.8 g ethyl acetate (Fisher Scientific Fair Lawn, N.J.) Then the organic phase (solution B) is prepared by dissolving 27.1 g of high viscosity 75:25 dl (polylactide-co-glycolide), (Medisorb Technologies International, L.P., Cincinnati, Ohio) in 99.3 g ethyl acetate and 99.1 g benzyl alcohol. Once the polymer is completely dissolved, 18.1. g risperidone base (Janssen Pharmaceutica, Beerse, Belgium) is added dissolved in the polymer solution. The exposure time of the dissolved risperidone with the polymer is kept to a minimum (<10 minutes). Solutions A and B are then pumped through a ¼ inch diameter static mixer (Cole-Parmer L04667-14) via a gear drive pump and head (Cole-Parmer L07149704, L07002-16) at flow rates of 198 and 24 mL/minute, respectively, and into a quench medium (wash) composed of 55 liters of water for injection containing 1,375.6 g of ethyl acetate, 92.4 g (0.02 Molar) of anhydrous sodium bicarbonate, and 116.6 g (0.02 Molar) of anhydrous sodium carbonate (Mallinckrodt Specialty Chemicals, Paris, Ky.) at 12° C. The microparticles are allowed to stir in this first wash for 2 hours, then isolated by sieving with a 25 micron sieve. The product retained by the sieve is transferred to a second 20-liter wash of WFI at 12° C. After stirring in the second wash for 3 hours, the microparticles are isolated and size fractionated by sieving through a stainless-steel sieve column composed of 25 and 180 micron mesh sizes. The microparticles are dried overnight, then collected and weighed.

EXAMPLE 4

Lyophilization and Gamma Irradiation of Microparticles from Batches Prodex 2 and Prodex 3 (Samples Prodex 4A, Prodex 4B, and Prodex 4C)

Microparticles from batches Prodex 2 and Prodex 3 were lyophilized as follows. The microparticles were weighed into 5 cc serum vials. Then an aqueous vehicle composed of 0.75% CMC, 5% Mannitol, and 0.1% Tween 80 was added to the vials. The microparticles were suspended in the vehicle by agitation, then quickly frozen in a dry ice/acetone bath. The vials were then lyophilized in a pilot-scale lyophilizer (Dura Stop Microprocessor Control, FTS Systems, Inc., Stone Ridge, N.Y.) employing a ramped 30° C. maximum temperature cycle for 50 hours. Samples Prodex 4A and Prodex 4C were lyophilized samples from Prodex 2 and Prodex 3, respectively. Sample Prodex 4B was lyophilized from Prodex 2 that had been subsequently sterilized by 2.2 MRad gamma irradiation from a $^{60}$Co source.

In Vitro Dissolution Studies

In vitro dissolution studies were conducted on Prodex 2, Prodex 3, Prodex 4A, Prodex 4B, and Prodex 4C. Real time and accelerated methodologies were used. The equipment consisted of a Hanson research 6-cell USP paddle (Method II) dissolution apparatus interfaced with a spectrophotometer and data station. Receiving media were continuously recirculated from each cell to flow cells inside the spectrophotometer. The absorbance of the receiving media was monitored at 236 nm for quantification of risperidone.

Figure 5:
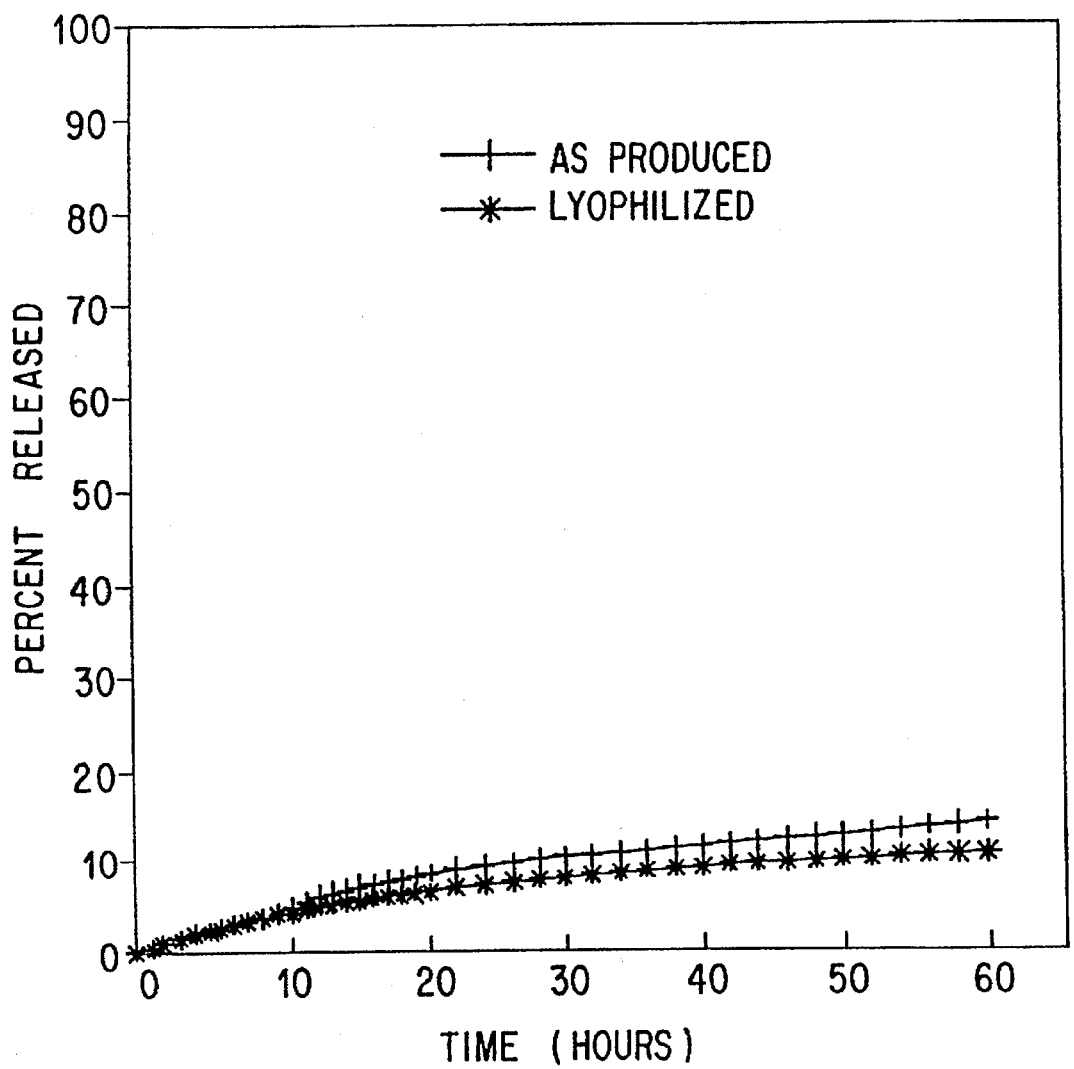
FIG. 5 depicts a graph of in vitro dissolution data for risperidone microparticles of batch Prodex 3, both as produced and lyophilized.
Figure 6:
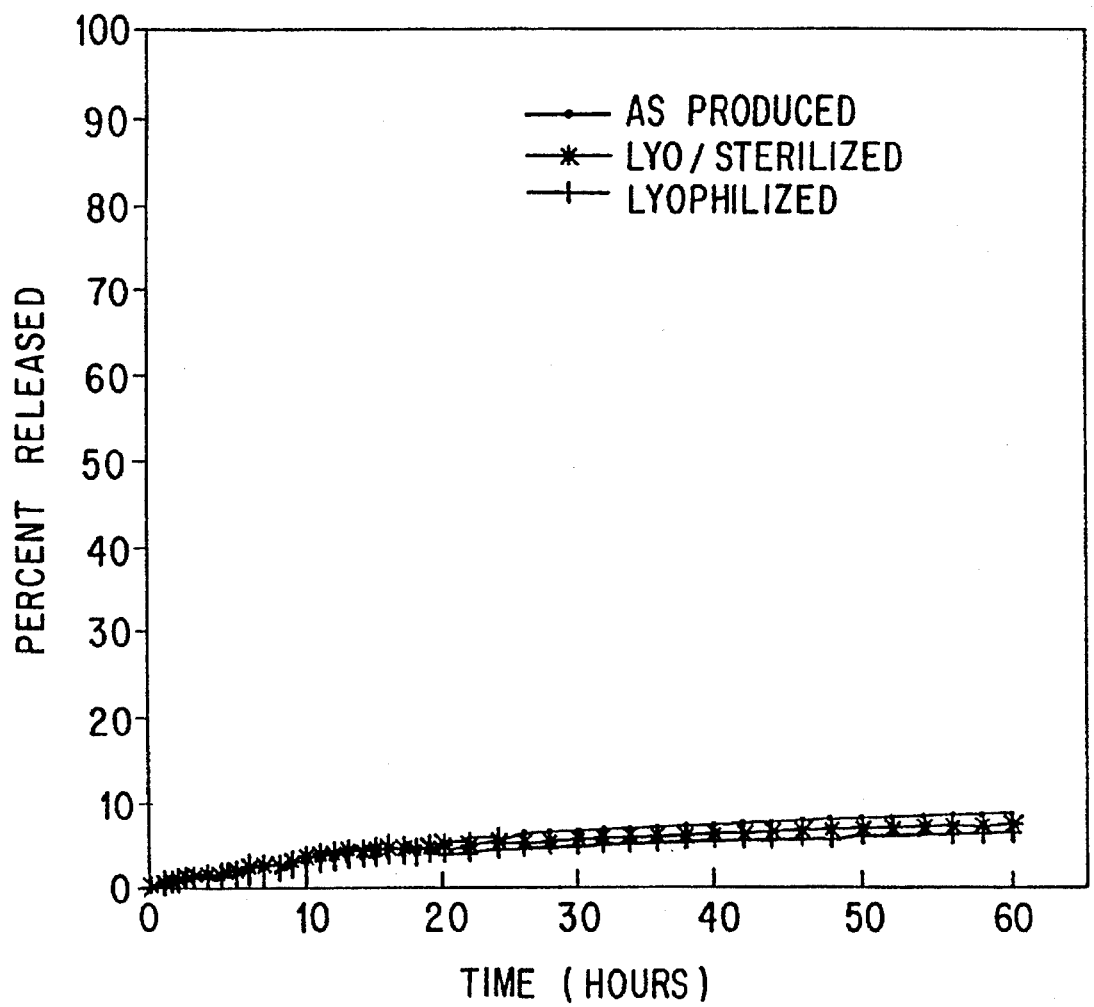
FIG. 6 depicts a graph of in vitro dissolution data for risperidone microparticles of batch Prodex 2, both as produced and lyophilized.

The real time model measured the release rates of microparticles into a receiving medium consisting of 50 mM tris buffer at pH 7.4 at 37° C. Risperidone was found to have sufficient solubility ($\geq 0.5$ mg/mL) to allow in vitro experiments with this receiving medium. The amount of risperidone was kept below 20% of saturation to provide infinite sink conditions. Data are shown in FIGS. 5 and 6.

Figure 7:
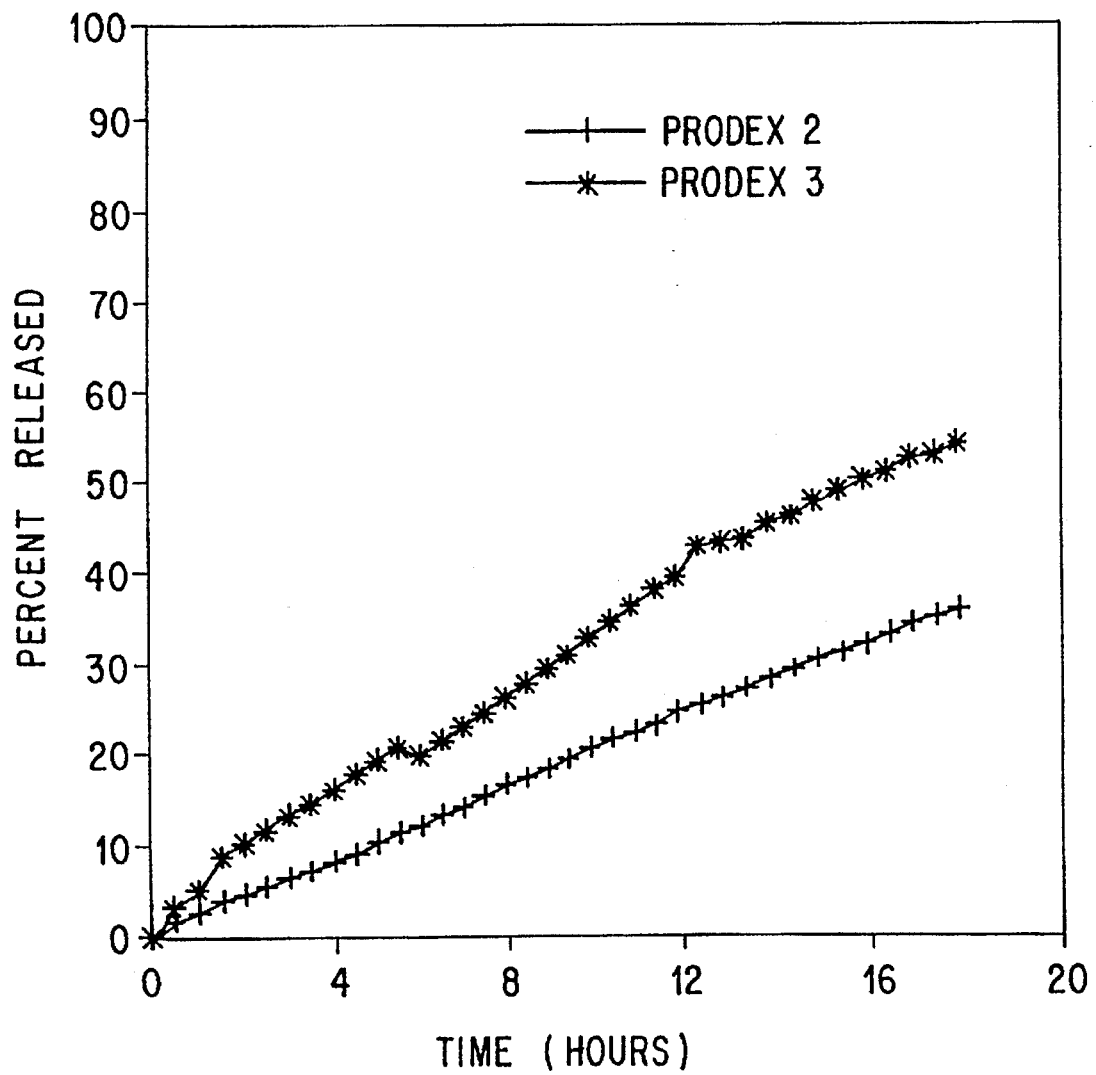
FIG. 7 depicts a graph of accelerated in vitro dissolution data for risperidone microparticles of batches Prodex 3 and Prodex 2.

An accelerated model was also developed. A receiving medium of 27.5 wt % ethanol in WFI was used. Results are shown in FIG. 7.

Animal Dosing and Blood Sampling

In vivo studies in dogs were conducted on product provided as dry microparticles (Prodex 2, Prodex 3) and in lyophilized form (Prodex 4A, Prodex 4B, Prodex 4C). The dry microparticles were syringe-loaded and resuspended in the syringe with an injection vehicle comprised of 2.5 wt % carboxymethyl cellulose (CMC). The lyophilized samples (Prodex 4A, Prodex 4B, Prodex 4C) were reconstituted in WFI prior to injection.

Male and female dogs, weighing 11.6±2.3 kg, were divided into groups of three dogs each. The dogs were housed in groups of three and fed according to standard laboratory conditions.

The appropriate volumes of the respective depot formulations were dosed intramuscularly into the biceps femoralis of the left hind limb at the level of the thigh of the dogs at a dose of approximately 2.5 mg/kg risperidone.

Blood samples (5 ml on EDTA) were taken from one of the jugular veins at 0 (predose), 1, 5, and 24 hours after dosing and also on days 4, 7, 11, 14, 18, 23, 25, 28, 32, 35, 39, 42, 46, 49, 53, and 56 at the time of the apomorphine vomiting test. The apomorphine test was described by P. A. J. Janssen and C. J. E. Niemegeers in Arzneim.-Forsch. (Drug Res.), 9:765–767 (1959). If, during the course of the experiments, each of the three dogs of a group no longer showed protection against apomorphine-induced vomiting, blood sampling was discontinued. Blood samples were centrifuged at 3000 rpm for 10 min and plasma was separated. The plasma samples were stored at $\leq 20°$ C. until analysis.

Plasma samples were analyzed for risperidone (RISP) and for 9-hydroxyrisperidone (9-OH RISP) using radioimmunoassay (RIA). For the plasma samples analyzed with RIA, two different RIA procedures were used, one for unchanged risperidone and the other for the active moiety (sum of risperidone and 9-hydroxy-risperidone, not to be confused with the term "active agent" used elsewhere herein). For the latter plasma samples, the concentrations of 9-hydroxy-risperidone were calculated as the difference between the concentrations of the active moiety and those of risperidone. The quantification limits for the RIA methods were 0.20 ng/ml for risperidone and 0.50 ng/ml for the active moiety.

For each of the formulations, mean (±S.D., n=3) plasma concentrations of risperidone, 9-hydroxy-risperidone, and of the active moiety, were calculated. Ratios of the plasma concentrations of 9-hydroxy-risperidone to those of risperidone were calculated where possible. Peak plasma concentrations and peak times of risperidone, 9-hydroxy-risperidone, and their sum were determined by visual inspection of the data. AUC ("area under the curve") values of risperidone and 9-hydroxy-risperidone were calculated between zero time and time using the trapezoidal rule. The time t is the last time point at which concentrations of risperidone or 9-hydroxy-risperidone were higher than the limit of quantification in at least 1 out of 3 dogs. For dogs belonging to the same formulation group, AUCs were calculated up to the same end-time t, using the value of the quantification limit, if one concentration was lower than the quantification limit. If two consecutive concentrations were lower than the quantification limit, the concentration of the earlier sampling point was set equal to the quantification limit, and the concentration of the later sampling point was taken as zero. The AUCs were not extrapolated to infinity. The AUC of the active moiety was calculated as the sum of the AUCs of risperidone and 9-hydroxy-risperidone.

Figure 8:
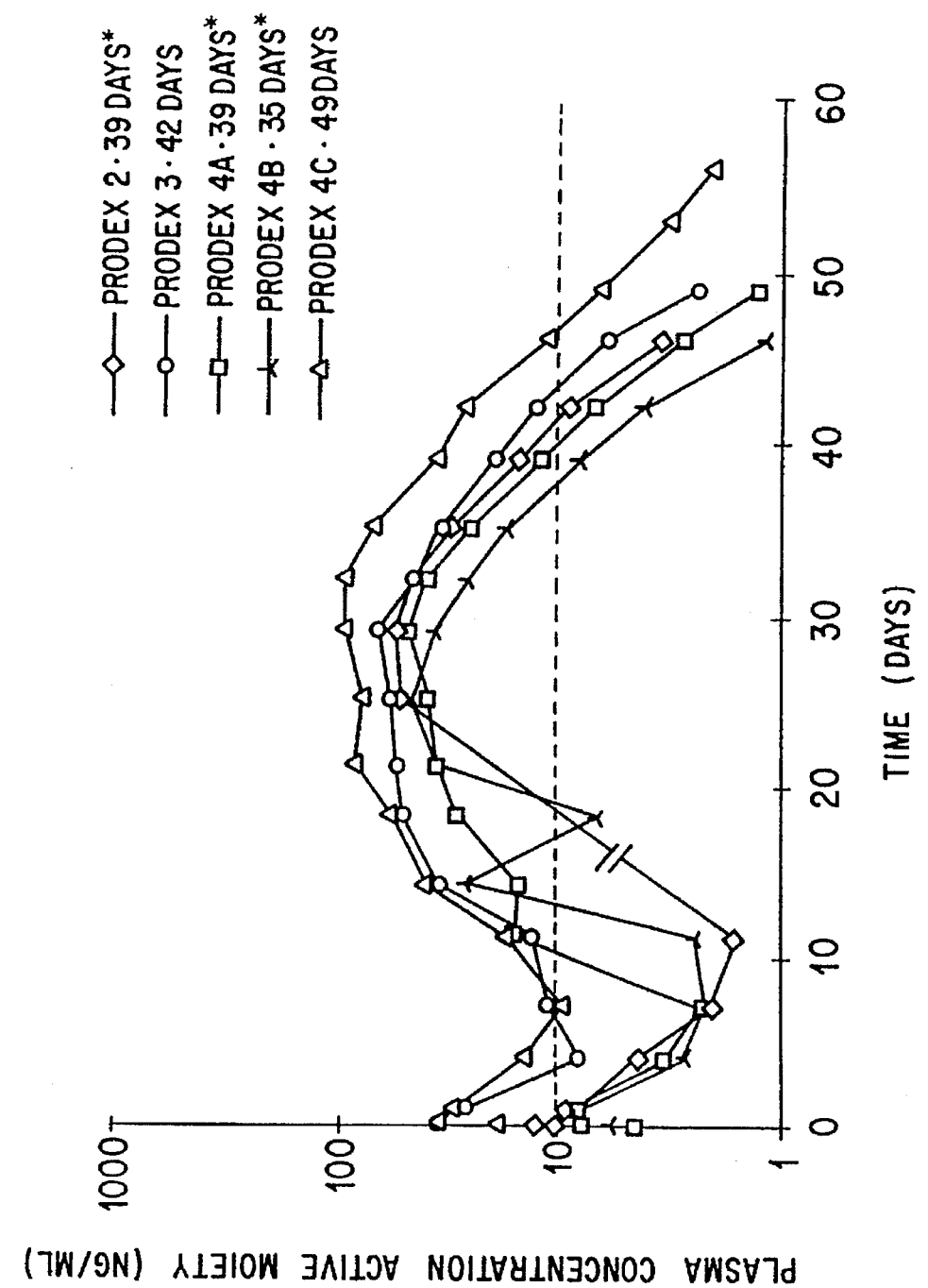
FIG. 8 depicts a graph of mean (n=2) plasma concentration-time curves for an active moiety (sum of risperidone and 9-hydroxy risperidone) after single intramuscular administration to beagle dogs of risperidone depot formulations at an approximate dose of 2.5 mg/kg. The period of anti-emetic activity (in at least 2 out of 3 dogs) in the apomorphine vomiting test is given in the legend for each of the formulations. An asterisk (*) indicates that the anti-emetic activity is interrupted in at least 2 out of 3 dogs at the beginning of the study. The broken line indicates an approximate lowest minimum plasma concentration necessary for anti-emetic activity. The // sign indicates that for formulation Prodex 2 no blood was sampled on days 14, 18, and 21.

Mean or median plasma concentrations and/or pharmacokinetic parameters of risperidone, 9-hydroxy-risperidone, and the active moiety for formulations Prodex 2/3/4A/4B/4C, are given in Table 1. Mean plasma concentration-time curves for formulations Prodex 2/3/4A/4B/4C are shown in FIG. 8. For each of the formulation groups, results are first discussed for risperidone, then for 9-hydroxy-risperidone, and last for the active moiety. For the active moiety, plasma concentrations are related to the anti-emetic effect in the apomorphine vomiting test.

After administration of formulations Prodex 2 up to Prodex 4C, mean peak plasma levels of risperidone were low. They were attained at largely different time points. The further release of risperidone from the different formulations proceeded gradually and was long-lasting. This resulted in low plasma concentrations of both risperidone and its metabolite. Mean peak times for 9-hydroxy-risperidone all ranged from 26 to 30 days. The plasma concentration-time profile of the active moiety was similar for formulations Prodex 2 up to Prodex 4C. At the beginning of the experiment, plasma concentrations of the active moiety showed a peak within 1 or 2 days, due to a rapid initial release of risperidone. The peak was followed by a decrease of the concentrations with a dip at 5–8 days. From day 8 on, concentrations increased again until day 20, after which time they remained at a more or less constant level during a period of, on average, 15 days. During this period, for each of the formulations, concentrations of the active moiety showed a second peak and concentrations were higher than for the first peak. The anti-emetic activity lasted 35 to 42 days for formulations Prodex 2, Prodex 4A, and Prodex 4B. For formulation Prodex 4C, it lasted 49 days, but without interruption in any of the dogs. The longest activity of formulation Prodex 4C paralleled the highest $C_{max}$, $T_{max}$, and $AUC_{0-t}$ for the active moiety, in comparison with the other 4 formulations of the same group.

The duration of action of these microparticle-based risperidone formulations in the apomorphine-induced emesis test in dogs was also studied. Neuroleptics antagonized apomorphine-induced emesis by blocking dopamine $D_2$ receptors in the area postrema of the fourth ventricle. The test is generally used to predict the onset and duration of antipsychotic action of neuroleptics in man (Janssen et al., Arzneim.-Forsch./Drug Res. 10:1196–1206 (1965); Niemegeers et at., Life Sci. 24:2201–2216 (1979)). 9-OH-risperidone has a pharmacological profile that is virtually identical to that of its parent compound. Parent compound and active metabolite constitute together the "active moiety" that determines the biological activity of risperidone.

Apomorphine was administered subcutaneously at 0.31 mg/kg to the dogs twice a week, during the whole course of the experiment. The dogs were observed for vomiting during a 1-hour period after the administration of apomorphine. Complete absence of emesis for 1 hour after apomorphine challenge was considered to reflect significant anti-emetic activity. The duration of the anti-emetic action was defined as the time interval during which 2 out of 3 dogs were protected from emesis.

The formulations were injected in a volume of 0.5 mL into the biceps femoralis of one of the hind limbs at the level of the thigh. At several time intervals after the intramuscular injection, blood samples were taken and, immediately thereafter, the dogs were challenged with a dose of apomorphine. Complete absence of emesis within 1 h after apomorphine challenge (which is never observed in control animals; n>1000) was considered to reflect significant anti-emetic activity.

Table 2 indicates whether the dogs were protected (+) or not protected (−) from apomorphine-induced emesis at the various time intervals after intramuscular injection of the depot formulations. All formulations showed an immediate onset of anti-emetic action.

TABLE 1

Mean (±S.D.; n = 3) or median plasma concentrations and mean (±S.D.; n = 3) pharmacokinetic parameters of risperidone, 9-hydroxy-risperidone, and their sum (= the "active moiety") after intramuscular administration of risperidone depot formulations at 2.5 mg/kg to beagle dogs.

| Time (days) | Prodex 2 | | Prodex 3 | | Prodex 4A | |
|---|---|---|---|---|---|---|
| | RISP | 9-OH RISP | RISP | 9-OH RISP | RISP | 9-OH RISP |
| 0 | ≦0.20 | ≦0.50 | ≦0.20 | ≦0.50 | ≦0.20 | ≦0.50 |
| 0.042 (1 h) | 8.36 ± 1.06 | 4.17 ± 1.71 | 21.4 ± 8.8 | 14.4 ± 9.1 | 3.25 ± 0.57 | 1.18 ± 0.50 |
| 0.208 (5 h) | 2.87 ± 0.20 | 7.34 ± 2.02 | 7.55 ± 3.38 | 27.4 ± 22.0 | 2.61 ± 0.60 | 5.13 ± 1.08 |
| 1 | 1.25 ± 0.72 | 6.92 ± 3.88 | 2.90 ± 1.70 | 23.0 ± 17.8 | 1.13 ± 0.24 | 7.82 ± 3.55 |
| 4 | 0.67 ± 0.61 | 4.36 ± 3.32 | 1.22 ± 0.77 | 6.58 ± 3.07 | 0.74 ± 0.38 | 2.54 ± 1.20 |
| 7 | 0.35* | 1.65 ± 1.24 | 1.96 ± 1.70 | 8.79 ± 6.72 | 0.39* | 1.90 ± 1.52 |
| 11 | 0.41 ± 0.15 | 1.16 ± 0.35 | 1.52 ± 0.91 | 11.2 ± 11.7 | 2.40 ± 3.55 | 12.7 ± 20.2 |
| 14 | —** | —** | 4.36 ± 1.99 | 29.4 ± 25.0 | 2.23 ± 1.19 | 12.6 ± 15.0 |
| 18 | — | — | 6.33 ± 2.48 | 44.1 ± 35.4 | 4.28 ± 1.41 | 23.3 ± 12.5 |
| 21 | — | — | 8.61 ± 2.25 | 44.8 ± 26.3 | 6.97 ± 1.57 | 27.1 ± 11.3 |
| 25 | 6.79 ± 1.74 | 44.6 ± 13.6 | 9.08 ± 3.95 | 47.9 ± 19.5 | 6.03 ± 1.50 | 32.3 ± 2.8 |
| 29 | 6.84 ± 3.19 | 46.0 ± 15.1 | 9.26 ± 5.27 | 54.2 ± 33.6 | 6.52 ± 1.40 | 40.2 ± 3.6 |
| 32 | 4.97 ± 1.89 | 39.5 ± 36.6 | 5.60 ± 2.78 | 38.8 ± 25.2 | 3.81 ± 1.72 | 35.2 ± 16.3 |
| 35 | 3.61 ± 1.84 | 25.8 ± 11.5 | 4.70 ± 3.39 | 28.4 ± 21.9 | 2.55 ± 1.31 | 22.1 ± 14.4 |
| 39 | 1.44 ± 0.51 | 13.0 ± 7.1 | 2.01 ± 1.47 | 16.4 ± 9.6 | 1.13 ± 0.82 | 10.4 ± 6.4 |

TABLE 1-continued

Mean (±S.D.; n = 3) or median plasma concentrations and mean (±S.D.; n = 3) pharmacokinetic parameters of risperidone, 9-hydroxy-risperidone, and their sum (= the "active moiety") after intramuscular administration of risperidone depot formulations at 2.5 mg/kg to beagle dogs.

| | | | | | | |
|---|---|---|---|---|---|---|
| 42 | 1.05 ± 0.45 | 7.73 ± 3.77 | 1.31 ± 0.79 | 10.7 ± 6.5 | 0.68* | 6.08 ± 4.26 |
| 46 | ≦0.20* | 2.94 ± 1.35 | 0.45* | 5.55 ± 4.04 | ≦0.20* | 2.48 ± 1.81 |
| 49 | — | — | 0.23* | 2.13 ± 1.34 | ≦0.20 | 1.23* |
| 53 | — | — | — | — | — | — |
| 56 | — | — | — | — | — | — |
| Cmax (ng/ml) | 8.61 ± 1.41 | 61.0 ± 19.7 | 21.4 ± 8.8 | 56.3 ± 32.2 | 7.75 ± 0.78 | 43.9 6.6 |
| Tmax (days) | 10 ± 17 | 29 ± 4 | 0.042 ± 0.000 | 26 ± 2 | 25 ± 4 | 30 ± 2 |
| AUC0-t (ng · h/ml) | 3212 ± 914 | 21496 ± 4854 | 5048 ± 2397 | 30632 ± 19866 | 3280 ± 576 | 19632 ± 8274 |
| t (days) | 46 | 46 | 49 | 49 | 46 | 49 |

| | RISP + 9-OH RISP | RISP + 9-OH RISP | RISP + 9-OH RISP |
|---|---|---|---|
| Cmax (ng/ml) | 67.3 ± 19.8 | 66.0 ± 37.0 | 49.6 ± 6.7 |
| Tmax (days) | 29 ± 4 | 26 ± 2 | 30 ± 2 |
| AUC0-t (ng · h/ml) | 24708 ± 5341 | 35680 ± 22261 | 22912 ± 8822 |

| | Prodex 4B | | Prodex 4C | |
|---|---|---|---|---|
| Time (days) | RISP | 9-OH RISP | RISP | 9-OH RISP |
| 0 | ≦0.20 | ≦0.50 | ≦0.20 | ≦0.50 |
| 0.042 (1 h) | 3.32 ± 0.75 | 2.53 ± 0.79 | 15.5 ± 5.2 | 3.32 ± 2.18 |
| 0.208 (5 h) | 1.52 ± 0.33 | 5.56 ± 2.43 | 15.1 ± 7.7 | 19.2 ± 6.2 |
| 1 | 1.22 ± 0.58 | 7.10 ± 3.40 | 4.49 ± 1.04 | 25.0 ± 7.1 |
| 4 | 0.58* | 2.25 ± 1.00 | 2.00 ± 0.42 | 12.1 ± 2.5 |
| 7 | 0.35* | 1.78* | 1.47 ± 0.29 | 7.96 ± 0.74 |
| 11 | 0.53* | 1.87* | 3.23 ± 1.72 | 13.4 ± 4.6 |
| 14 | 4.06 ± 3.47 | 22.1 ± 20.3 | 7.67 ± 4.54 | 30.9 ± 17.8 |
| 18 | 1.41 ± 0.14 | 5.13 ± 0.85 | 8.15 ± 4.69 | 48.5 ± 34.5 |
| 21 | 7.22 ± 4.98 | 27.1 ± 21.1 | 13.1 ± 9.4 | 69.3 ± 41.4 |
| 25 | 5.39 ± 3.41 | 41.0 ± 29.7 | 8.37 ± 0.88 | 67.8 ± 28.0 |
| 29 | 4.66 ± 1.47 | 31.1 ± 13.3 | 13.8 ± 5.2 | 77.9 ± 17.7 |
| 32 | 3.50 ± 1.81 | 21.4 ± 9.8 | 10.3 ± 4.5 | 80.9 ± 51.3 |
| 35 | 1.91 ± 0.71 | 14.9 ± 4.5 | 7.58 ± 3.49 | 61.4 ± 15.1 |
| 39 | 0.67 ± 0.16 | 7.15 ± 2.47 | 3.90 ± 1.34 | 31.2 ± 10.7 |
| 42 | ≦0.20* | 3.83 ± 0.40 | 2.97 ± 1.35 | 23.2 ± 13.7 |
| 46 | ≦0.20* | 1.08 ± 0.53 | 0.68 ± 0.39 | 10.4 ± 6.3 |
| 49 | — | — | 0.26* | 6.04 ± 3.75 |
| 53 | — | — | ≦0.20* | 2.98 ± 2.39 |
| 56 | — | — | ≦0.20* | 1.89 ± 1.40 |
| Cmax (ng/ml) | 7.71 ± 4.23 | 42.6 ± 27.3 | 16.3 ± 6.6 | 95.4 ± 41.7 |
| Tmax (days) | 24 ± 5 | 26 ± 2 | 0.097 ± 0.096 | 30 ± 2 |
| AUC0-t (ng · h/ml) | 2648 ± 1199 | 15656 ± 8104 | 7424 ± 3018 | 46840 ± 19125 |
| t (days) | 46 | 46 | 56 | 56 |

| | RISP + 9-OH RISP | RISP + 9-OH RISP |
|---|---|---|
| Cmax (ng/ml) | 48.5 ± 29.8 | 108 ± 44 |
| Tmax (days) | 26 ± 2 | 30 ± 2 |
| AUC0-t (ng · h/ml) | 18311 ± 9222 | 54264 ± 22055 |

*Median value.
**No blood sampling from day 14 until day 25 of the experiment, due to absence of protection against apomorphine-induced vomiting. Concentrations in italics indicate antiemetic activity in at least 2 out of 3 dogs.

TABLE 2

Protection (+) or no protection (−) from apomorphine-induced emesis in dogs at successive time intervals after intramuscular administration of microparticle-based depot formulations of the antipsychotic risperidone at an approximate dose level of 2.5 mg/kg (continued from previous page)

| Form. | Prodex 2 | | | Prodex 3 | | | Prodex 4A | | | Prodex 4B | | | Prodex 4C | | |
|---|---|---|---|---|---|---|---|---|---|---|---|---|---|---|---|
| Dog Weight (kg) | 14.2 | 11.5 | 9.8 | 12.9 | 12.4 | 13.4 | 10.0 | 12.3 | 9.2 | 9.7 | 8.6 | 10.6 | 13.2 | 16.4 | 16.2 |
| Volume (ml/dog) | 0.53 | 0.53 | 0.53 | 0.53 | 0.53 | 0.53 | 0.53 | 0.53 | 0.53 | 0.53 | 0.53 | 0.53 | 0.53 | 0.53 | 0.53 |
| Dose (mg/kg) | 2.5 | 2.5 | 2.8 | 2.5 | 2.5 | 2.5 | 2.5 | 2.3 | 2.6 | 2.5 | 2.5 | 2.6 | 2.4 | 2.4 | 2.5 |
| Route | im | im | im | im | im | im | im | im | im | im | im | im | im | im | im |

TABLE 2-continued

Protection (+) or no protection (−) from apomorphine-induced emesis in dogs at successive time intervals after intramuscular administration of microparticle-based depot formulations of the antipsychotic risperidone at an approximate dose level of 2.5 mg/kg (continued from previous page)

| Form. | Prodex 2 | | | Prodex 3 | | | Prodex 4A | | | Prodex 4B | | | Prodex 4C | | |
|---|---|---|---|---|---|---|---|---|---|---|---|---|---|---|---|
| 1 h | + | + | − | + | + | + | + | + | + | − | + | + | + | + | + |
| 5 h | + | + | + | + | + | + | + | + | + | + | − | + | + | + | + |
| 1 d | + | + | + | + | + | + | + | + | + | + | + | + | + | + | + |
| 4 d | − | − | + | + | − | + | + | + | − | − | − | + | + | + | + |
| 7 d | − | − | − | − | + | + | − | − | − | − | − | + | + | + | + |
| 11 d | − | − | − | + | + | + | + | + | − | − | − | + | + | + | + |
| 14 d | | | | + | + | + | + | + | + | − | + | + | + | + | + |
| 18 d | | | | + | + | + | + | + | + | + | + | + | + | + | + |
| 21 d | | | | + | + | + | + | + | + | + | + | + | + | + | + |
| 25 d | + | + | + | + | + | + | + | + | + | + | + | + | + | + | + |
| 29 d | + | + | + | + | + | + | + | + | + | + | + | + | + | + | + |
| 32 d | + | + | + | + | + | + | + | + | + | + | + | + | + | + | + |
| 35 d | + | + | + | + | + | + | + | + | + | + | + | + | + | + | + |
| 39 d | − | + | + | + | − | + | + | + | − | − | − | − | + | + | + |
| 42 d | − | − | − | + | − | + | + | − | − | − | − | − | + | + | − |
| 46 d | − | − | − | + | − | − | − | − | − | − | − | − | + | + | − |
| 49 d | | Stop | | − | − | − | − | − | − | | Stop | | + | + | − |
| 53 d | | | | | Stop | | | Stop | | | | | − | + | − |
| 56 d | | | | | | | | | | | | | − | − | − |
| | | | | | | | | | | | | | | Stop | |

3 Injection volume: 0.5 ml/dog; the concentration of the microparticles was adapted to the body weight.

EXAMPLE 5

Figure 9:
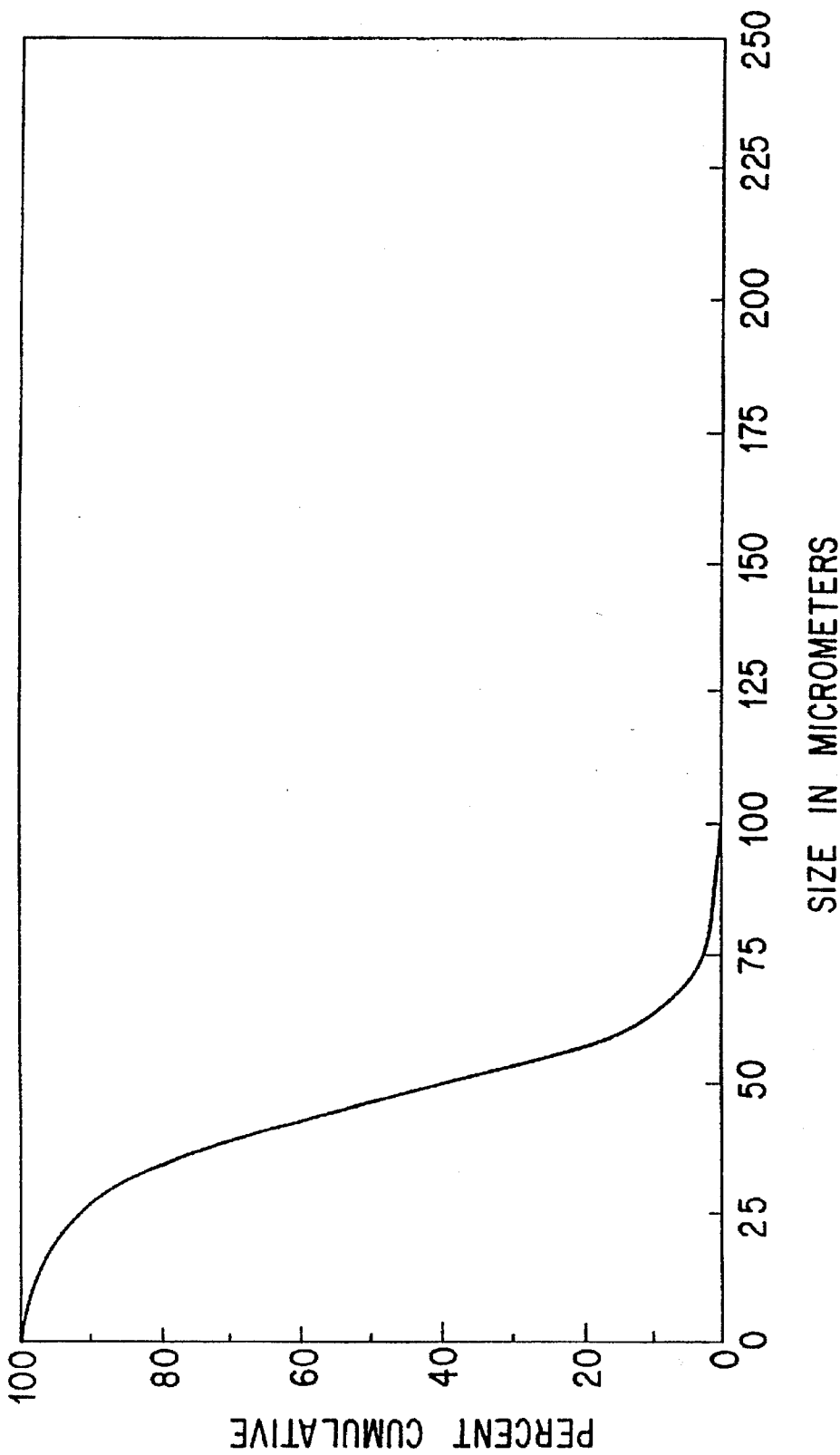
FIG. 9 depicts a graph of cumulative percent by microparticle size of estradiol benzoate loaded microparticles.
Figure 10:
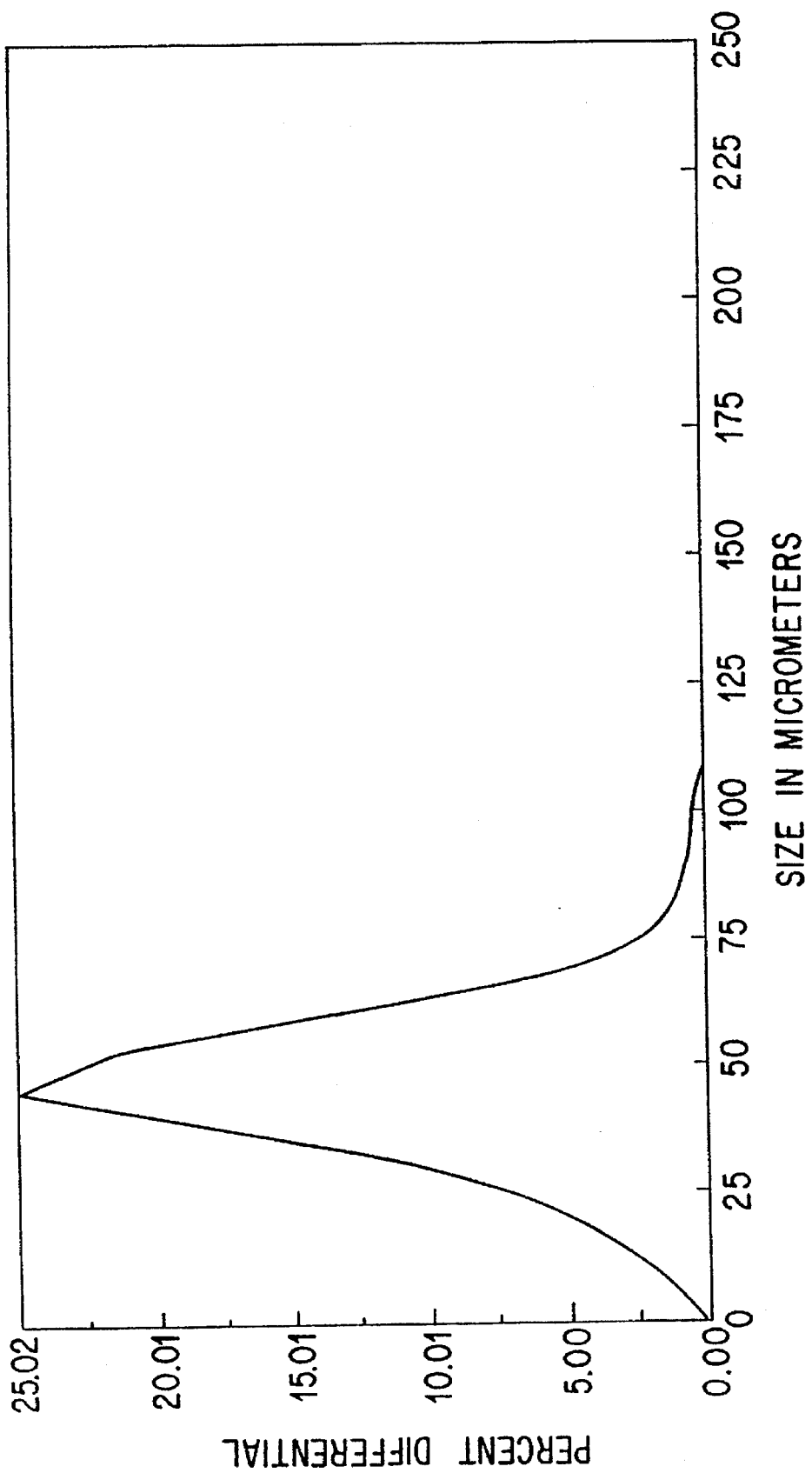
FIG. 10 depicts a graph of percent differential by microparticle size of estradiol benzoate loaded microparticles.

Preparation of 20% and 30% Theoretically Loaded Estradiol Benzoate Microparticles Table 3 shows the particle size distribution for experimental trials for 20% and 30% loaded microparticles. The particle size distribution is also shown in FIG. 9 which depicts the cumulative percent by microparticle size ("Volume Percent Greater") for one batch of 20% loaded microparticles. FIG. 10 depicts the percent differential by microparticle size ("Volume Differential") for one batch of 20% loaded microparticles. From this data, it can be seen that increasing the flow rate decreased particle size. No significant difference was seen between 12 and 24 element mixers. Increasing the aqueous or water phase:organic phase ratio narrows particle size distribution. Good microparticles were produced in the transitional flow range, Reynolds Number (Re) of 2000–4000.

Additional batches of 20% and 30% loaded microparticles were subsequently prepared. A 7 kg batch of 20% drug loaded microparticles was prepared using a ½" diameter×24 element static mixer (Cole-Parmer polypropylene disposable 04667, Cole-Parmer Instrument Company, Chicago, Ill.). The organic phase was comprised of 4.0% estradiol benzoite (active agent), 16.0% 85:15 dl PLGA (a copolymer of 85 mole % lactic acid and 15 mole % glycolic acid, polylactide-co-glycolide) and 80.0% ethyl acetate at 60°–70° C. The water phase was comprised of 1.0% polyvinyl alcohol, 5.0% ethyl acetate, and 94.0% water at 60°–70° C. The organic phase flow rate and the water phase flow rate were the same at 1100 ml/min. A Cole-Parmer 6231-26 pump with a 7001-80 head was used for both the organic phase and water phase. The resulting particle size distribution was 15%<25 μm, 14% 25–45 μm, 56% 45–90 μm, 12% 90–150 μm, and 3%>150 μm.

A 5 kg batch of 30% drug loaded microparticles was prepared using ½" diameter×24 element static mixer and ⅜" diameter×11, 12, and 24 element static mixer (Cole-Parmer disposable). The organic phase was comprised of 4.3% estradiol benzoate (active agent), 10.0% 85:15 dl PLGA, and 85.7% ethyl acetate at 60°–70° C. The same water phase was used as in the 20% loaded microparticles. The organic phase flow rate was 880 ml/min and the water phase flow rate was 1650 ml/min. The resulting particle size distribution was 44%<25 μm, 31% 25–45 μm, and 25%>45 μm.

Figure 11:
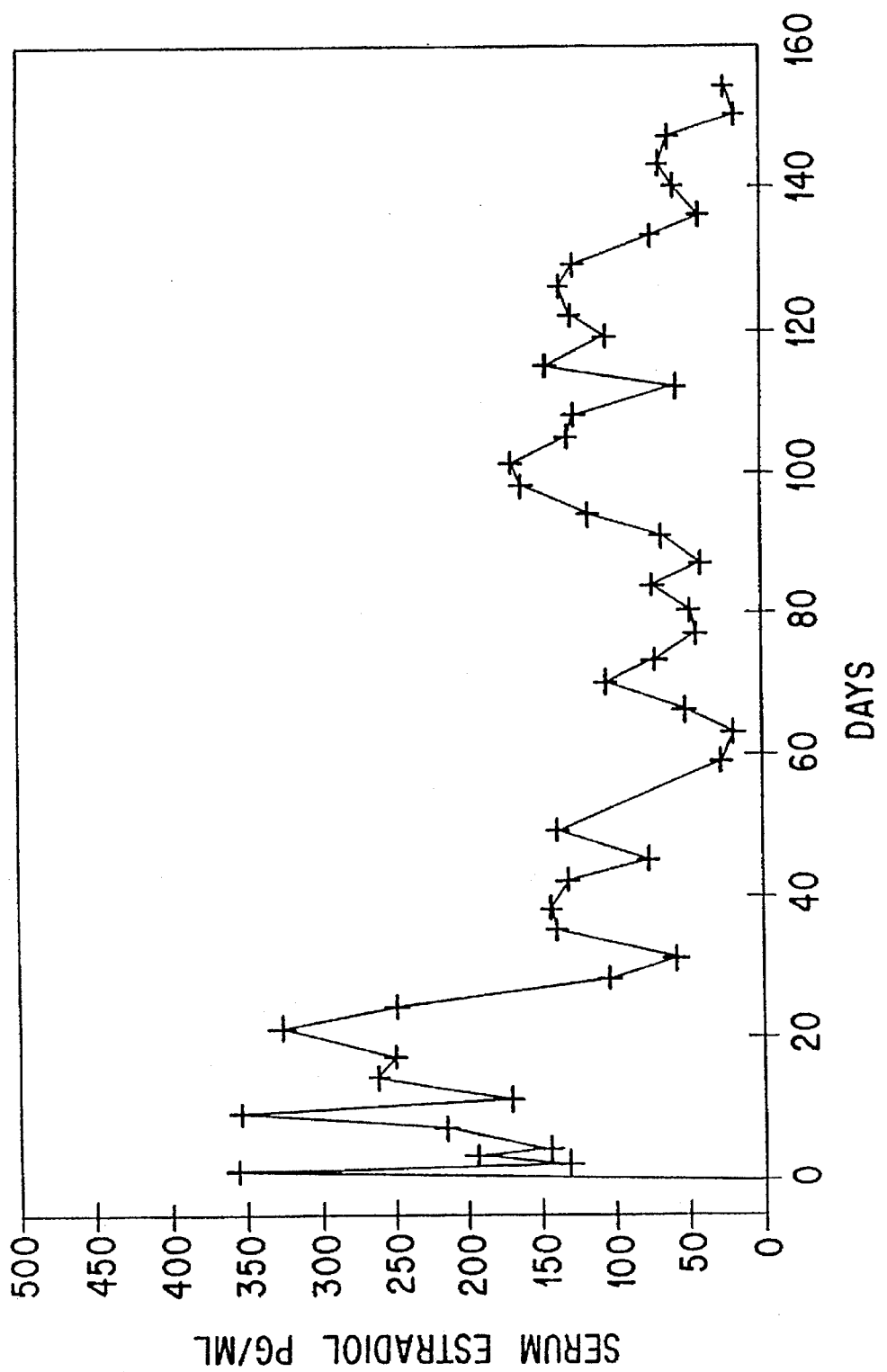
FIG. 11 depicts a graph of time release animal test data for estradiol benzoate loaded microparticles.

Estradiol benzoate loaded microparticles were weighed into conventional syringes and administered to young Holstein bull calves at a dose of 40 mg of active drug per animal. The microparticles were suspended in an aqueous carboxymethyl cellulose vehicle and injected at the base of the ear. Serum was collected and estradiol levels determined by radioimmunoassay; the results are shown in FIG. 11.

TABLE 3

Experimental Trials With Inline Static Mixers

| Flowrate | | | | Mixer | | | Size | |
|---|---|---|---|---|---|---|---|---|
| Water (ml/min) | Oil (ml/min) | Total (ml/min) | Ratio | Elements | dia (in) | vel. (ft/sec) | peak (um) | width (um) |
| 30% Drug Loaded Product | | | | | | | | |
| 200 | 200 | 400 | 1:1 | 11 | ⅜ | 0.30 | no spheres | |
| 400 | 400 | 800 | 1:1 | 11 | ⅜ | 0.61 | good spheres | |
| 500 | 500 | 1000 | 1:1 | 11 | ⅜ | 0.77 | 50 | 60 |
| 750 | 750 | 1500 | 1:1 | 11 | ⅜ | 1.15 | less than 25 | |

TABLE 3-continued

Experimental Trials With Inline Static Mixers

| Flowrate | | | | Mixer | | | Size | |
|---|---|---|---|---|---|---|---|---|
| Water (ml/min) | Oil (ml/min) | Total (ml/min) | Ratio | Elements | dia (in) | vel. (ft/sec) | peak (um) | width (um) |
| 400 | 400 | 800 | 1:1 | 12 | ⅜ | 0.61 | 70 | 125 |
| 500 | 500 | 1000 | 1:1 | 12 | ⅜ | 0.77 | 45 | 55 |
| 400 | 400 | 800 | 1:1 | 24 | ⅜ | 0.61 | 70 | 110 |
| 533 | 266 | 800 | 2:1 | 24 | ⅜ | 0.61 | 45 | 50 |
| 600 | 200 | 800 | 3:1 | 24 | ⅜ | 0.61 | 62 | 45 |
| 533 | 266 | 800 | 2:1 | 24 | ⅜ | 0.61 | 70 | 50 |
| 400 | 200 | 600 | 2:1 | 24 | ⅜ | 0.46 | 95 | 82 |
| 600 | 300 | 900 | 2:1 | 24 | ⅜ | 0.69 | 55 | 42 |
| 400 | 400 | 800 | 1:1 | 24 | ⅜ | 0.61 | 75 | 64 |
| 534 | 266 | 800 | 2:1 | 24 | ⅜ | 0.61 | 65 | 46 |
| 1166 | 638 | 1804 | 1.8:1 | 24 | ½ | 0.77 | 55 | 45 |
| 1300 | 726 | 2026 | 1.8:1 | 24 | ½ | 0.87 | 45 | 35 |
| 1520 | 792 | 2312 | 1.9:1 | 24 | ½ | 1.00 | 40 | 40 |
| 1650 | 880 | 2530 | 1.9:1 | 24 | ½ | 1.09 | 35 | 30 |
| 20% Drug Loaded Product | | | | | | | | |
| 1540 | 990 | 2530 | 1.6:1 | 24 | ½ | 1.09 | 55 | 50 |
| 1320 | 990 | 2310 | 1.3:1 | 24 | ½ | 1.00 | 60 | 50 |
| 1100 | 1100 | 2200 | 1:1 | 24 | ½ | 0.95 | 65 | 45 |

Note:
1. First four used peristaltic pump instead of gear pump.
2. Particle size by Hiac Royco except last two estimated from seiving Formulae
30% Oil Phase:     85.7% Ethyl acetate
(60–70 C.)         10.0% 85:15 dl PLGA
                   4.3% Estradiol Benzoate
20% Oil Phase:     80.0% Ethyl acetate
(60–70 C.)         16.0% 85:15 dl PLGA
                   4.0% Estradiol Benzoate
Water Phase:       94.0% Water for injection
(60–70 C.)         5.0% Ethyl acetate
                   1.0% Polyvinyl alcohol

EXAMPLE 6

Preparation of 40% Theoretically Loaded Trenbolone Acetate Microparticles

Nine batches of trenbolone acetate (TBA) microparticles were prepared by using a static mixer. Microparticles, containing 40% TBA and 5% butylated hydroxytoluene (BHT, used as an antioxidant) were prepared by the following procedure. PLGA (molar ratio of D,L-lactide to glycolide: 85:15, molecular weights by GPC: Mw=86,810; Mn=36,417), TBA, and BHT were dissolved in ethyl acetate (EtOAc) at 55° C. (ratio of EtOAc to PLGA: 10–20:1). EtOAc was heated to 55° C. and PLGA was added to EtOAc under fast stirring. After the polymer was dissolved, BHT and then TBA were dissolved in the polymer solution. Simultaneously, poly(vinyl alcohol) (PVA) water solution (3 wt. %) spiked with EtOAc (ratio of PVA solution to EtOAc: 10:1) was charged to a jacketed flask and heated to 55° C. When the temperature of the polymer-drug solution (organic phase) and PVA solution (aqueous phase) were constant, the polymer-drug solution and PVA solution were plumped separately to a static mixer (1 cm in diameter and 12 cm in length). The static mixer was manufactured by Cole-Parmer, model number 6-04667-06, and contained 12 mixing elements. The flow rate ratio of polymer-drug solution to PVA solution was varied from 1:1.2 to 1:2. The ratio of quenching water to EtOAc was 100–150:1. Quench water temperature was approximately 1° C. After being washed for 6 hours, the microparticles were sieved through a sieve column (25 µm, 90 µm, 150 µm, and 212 µm), and then dried.

Figure 12:
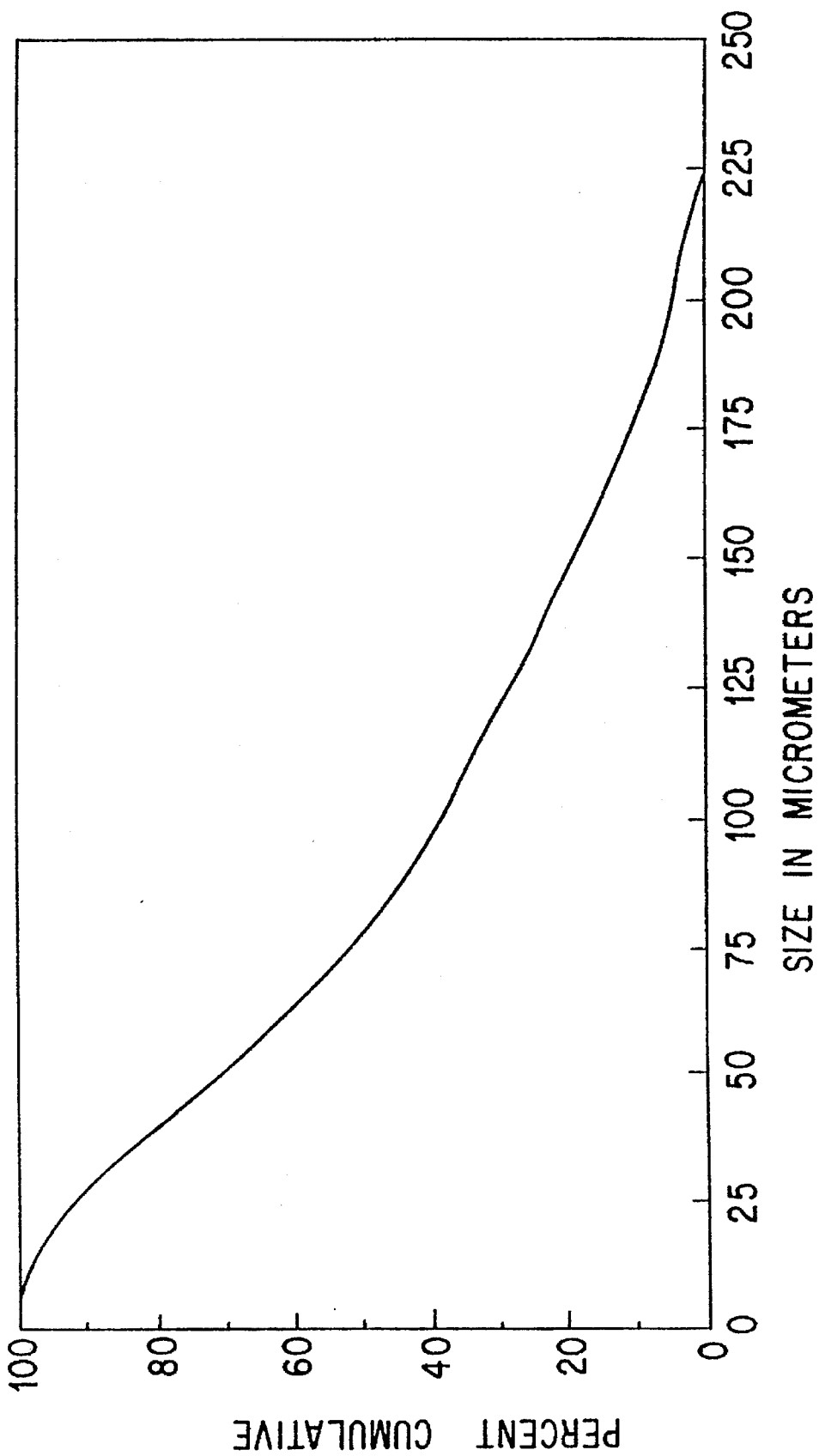
FIG. 12 depicts a graph of cumulative percent by microparticle size of trenbolone acetate loaded microparticles.

Particle size distribution of one batch of microparticles is depicted in FIG. 12.

EXAMPLE 7

Preparation of 46% Theoretically Loaded Testosterone Microparticles

A 1 kg batch of 46% testosterone loaded microparticles is prepared using a ¾" diameter×12 element static mixer (Koflo, M/N: ¾-TU-3-12RH-11, Koflo Corp., Cary, Ill.). The polymer/drug solution (organic phase) is prepared as follows. 506 gm of Testosterone USP is dissolved in a heated (65°–70° C.) solution of 594 gm of Medisorb® 75:25 dl PLGA (a copolymer of 75 mole % lactic acid and 25 mole % glycolic acid, polylactide-co-glycolide) (IV=0.68 dl/gm) in 3.683 kg ethyl acetate NF. The solution is filtered (0.2 µm) and maintained at 65°–70° C. The process water solution (aqueous phase) is prepared as follows 52 gm of PVA (Du Pont Elvanol® 51-05) is added to 9.75 kg of WFI and heated (65°–70° C.) until dissolved, and then filtered (0.2 µm). To this solution is added 626 gm of filtered (0.2 µm) ethyl acetate NF. The solution is maintained at 65°–70° C. The quench liquid is comprised of 750 liters WFI, maintained at 0°–4° C.

The organic phase is pumped through the static mixer at a flow rate of 2150 cc/min, and the aqueous phase at flow rate of 4300 cc/min. After 1 hour of quench, the material is passed through 45 and 150 µm screens. The 45–150 µm portion is vacuum dried with agitation for 36 hours at ambient temperature. The process yield is 875 gm of testosterone loaded microparticles.

Figure 13:
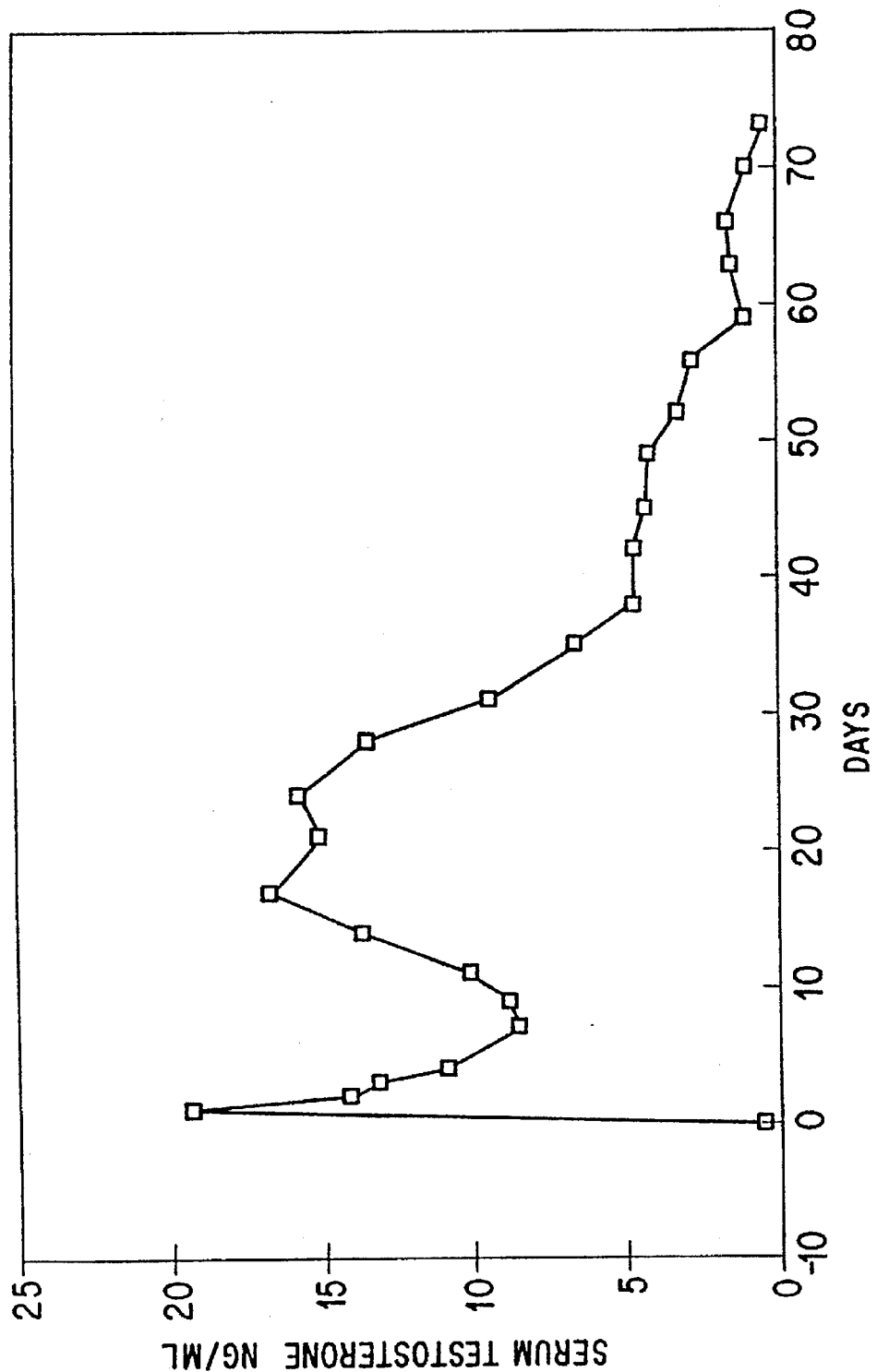
FIG. 13 depicts a graph of time release animal test data for testosterone loaded microparticles.
Figure 14A:
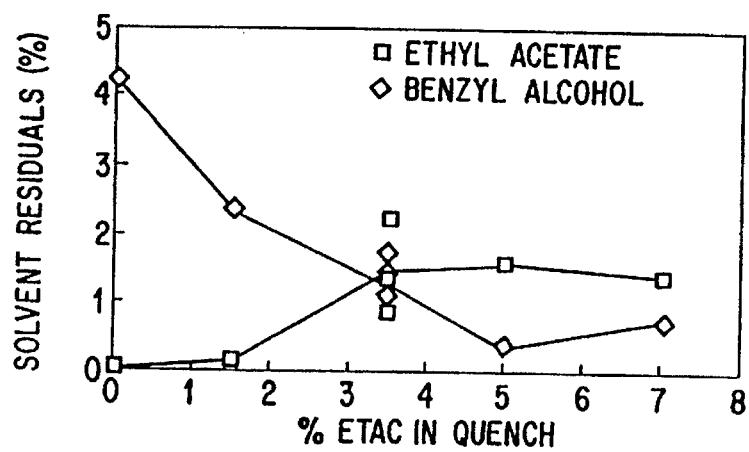
FIGS. 14A-C depicts three graphs showing the effect of spiking the quench liquid with ethyl acetate on norethindrone (NET) microparticle characteristics.
Figure 14B:
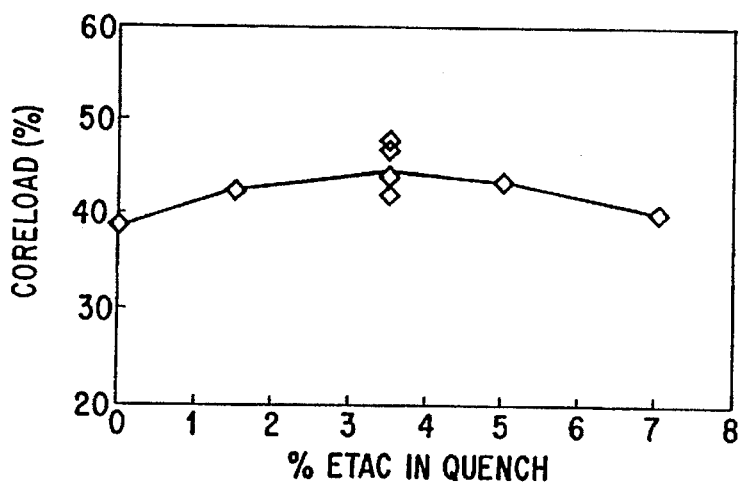
Figure 14C:
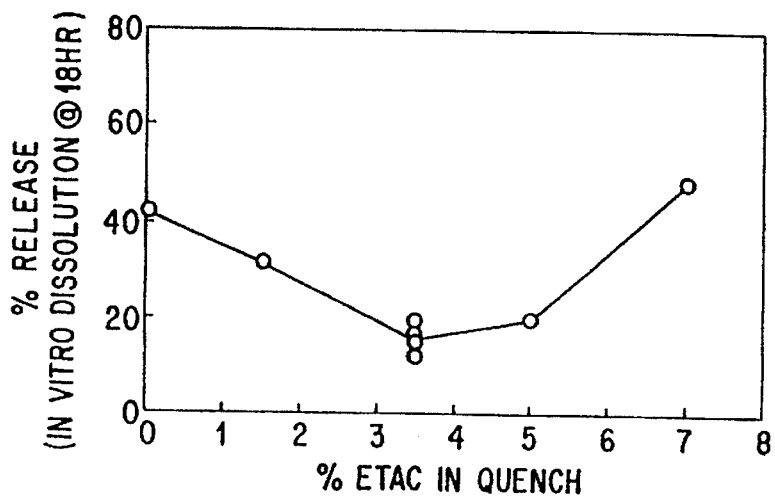
Figure 15A:
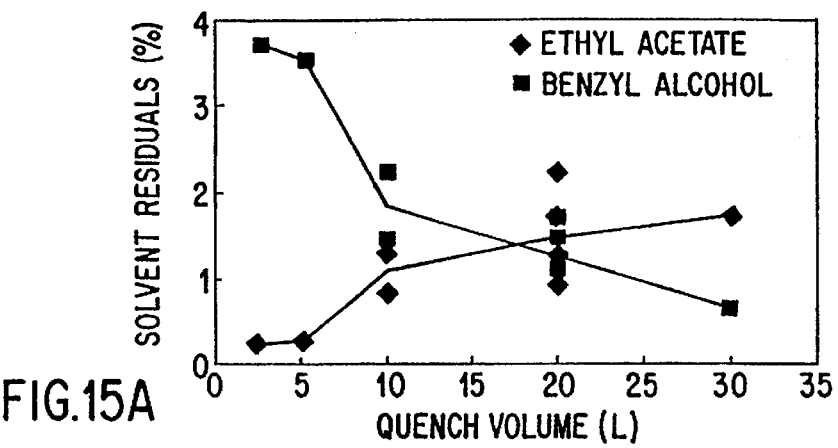
FIGS. 15A-C depict three graphs showing the effect of quench volume on NET microparticle characteristics.
Figure 15B:
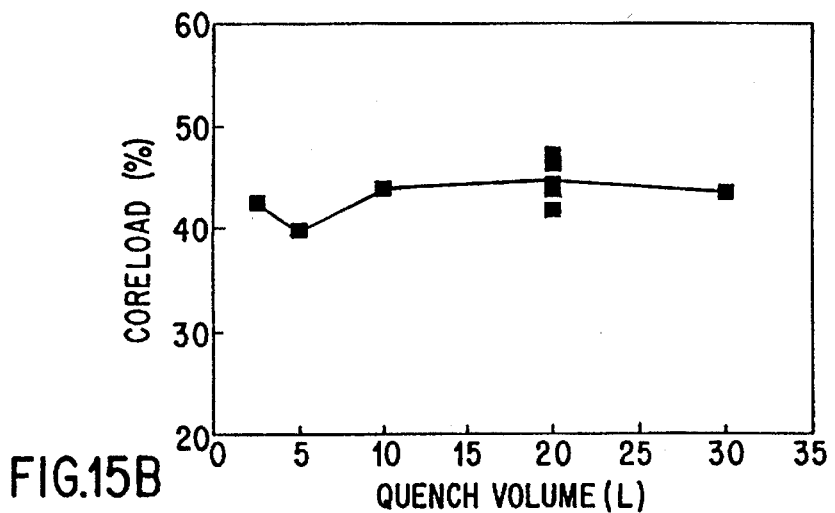
Figure 15C:
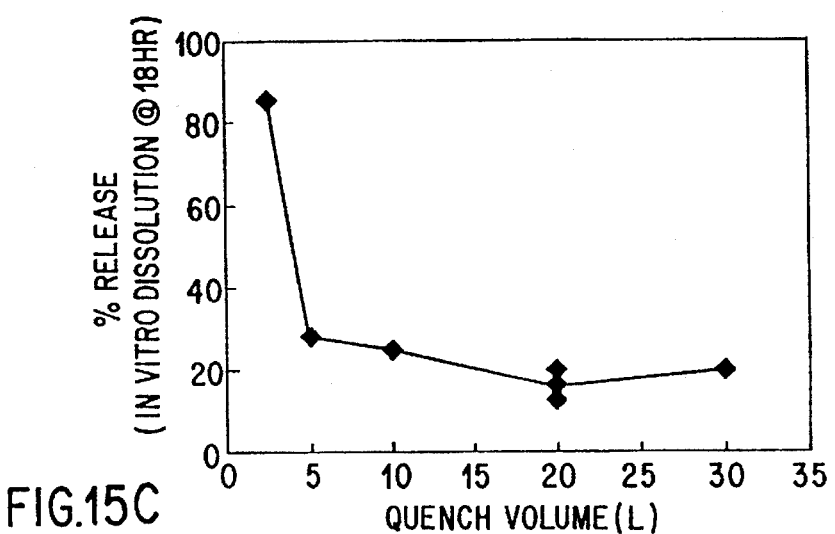

The 46% loaded microparticles were used to prepare 125-mg testosterone doses (suspension filled and lyophilized) which were administered to baboons. Time release data are shown in FIG. 13.

EXAMPLE 8

Preparation of 1.7% Theoretically Loaded rgp 120 Microparticles

A 10 gm batch of 1.7% rgp 120 (a glycoprotein) loaded microparticles is prepared using a ¼" diameter×5 element static mixer (Koch, ¼" SMV-DY; ¼" Dia, 5 elements, 316SS, Koch Engineering Company, Inc, Wichita, Kans.). The polymer/drug solution (organic phase) is prepared as follows. A primary emulsion is made by adding 3 cc of 56 mg/ml rgp120 in Tris buffer (20 mM Tris, 120 mM NaCl, pH 7.4) to 10 gm of Medisorb, 65:35 dl PLGA (a copolymer of 65 mole % lactic acid and 35 mole % glycolic acid, polylactide-co-glycolide) (IV=0.61) in 47 gm of ethyl acetate. The emulsion is formed by sonication (Vibra cell sonicator, 600 watt, 20 sec, 50% power with ½" probe). The emulsion is maintained at 0°–4° C. The process water solution (aqueous phase) is prepared as follows. 225 gm of PVA (Air Products, Vinol 205) is added to 2025 gm of WFI, and heated (65°–70° C.) until dissolved. To this solution, 250 gm of ethyl acetate is added. The solution is maintained at 0°–4° C. The quench liquid is comprised of 12 liters of water, maintained at 0°–4° C.

The organic phase is pumped through the static mixer at a flow rate of 40 cc/min, and the aqueous phase at a flow rate of 1500 cc/min. After 1 hour of quench, the microparticles are passed through 150 and 20 µm screens. The 20–150 µm portion is washed with 13 liters of 0.1% Tween 20 solution 0°–4° C. and then lyophilized. The process yield is 3.09 gm of rgp 120 loaded microparticles.

EXAMPLE 9

Preparation of 60% Theoretically Loaded Ivermectin Microparticles

To prepare a 35 g batch of 60% theoretically loaded ivermectin microparticles, the dispersed phase (Solution A) is prepared by dissolving 21.03 g of ivermectin in 116.72 g of polymer solution comprised of 9.5% 65:35 dl (polylactide-co-glycolide), (Medisorb Technologies International, L.P., Cincinnati, Ohio) and 90.5% ethyl acetate (Fisher Scientific, Fair Lawn, N.J.) at 52° C. Then 1300 g of the continuous phase (solution B) comprised of 1% poly (vinyl alcohol), (Vinol 205, Air Products and Chemical Inc., Allentown, Pa.) and 99% WFI is weighed out and heated to 52° C. Then solutions A and B are pumped through the static mixer (Cole-Parmer part number L04667-14) via a gear drive pump and head (Cole-Parmer L07149-04, L07002-16) at flow rates of 88 and 165 ml/minute, respectively, and into a quench liquid composed of 35 liters CWFI (Cold Water For Injection) at 8° C. The microparticles are allowed to stir for about 20 minutes, then isolated by sieving the quench through a 25 µm sieve. The product retained by the sieve is transferred to a wash of 20 liters stirring CWFI at 8° C. After stirring for 2 hours, the microparticles are isolated and size fractionated by sieving the wash through 25 and 212 micron sieves. The microparticles are air-dried overnight and collected.

EXAMPLE 10

Preparation of 60% Theoretically Loaded Bupivacaine Base Microparticles

An excess of the aqueous continuous phase is prepared by adding 216.1 g ethyl acetate (Fisher Scientific, Fair Lawn, N.J.) to 3780.3 g of a 5% aqueous poly (vinyl alcohol) solution (Vinol 205, Air Products and Chemical Inc., Allentown, Pa.) and adjusting to pH 8.5 with 1N NaOH at ambient temperatures. The organic phase is then prepared by dissolving 8.05 g low viscosity 50:50 dl polylactide-co-glycolide (a copolymer of 50 mole % lactic acid and 50 mole % glycolic acid) (Medisorb Technologies International, L.P.), and 12.05 g bupivacaine base (Aceto Corporation, Lake Success, N.Y.) in 92.1 g ethyl acetate at room temperature. The aqueous and organic solutions are then simultaneously pumped through a 24 element, ¼" diameter static mixer (Cole-Parmer L04667) via gear drive pumps and heads (Cole-Parmer L07144-05, pump; L07002-16, head, aqueous; L07062-26 head, organic) at flow rates of 233 and 116 ml/minute, respectively, into a quench liquid of 12 liters of water for injection adjusted to pH 8.5 at room temperature. The microparticles are stirred in the quench water for 1 hour then isolated by sieving through 25, 45, and 90 µm mesh stainless steel sieves. The microparticles are air dried overnight and protected from light prior to weighing.

EXAMPLE 11

Preparation of 17.5% Theoretically Loaded Pig Albumin Microspheres

A 2 gm batch of pig albumin loaded microspheres was prepared using a ½" diameter×12" long static mixer. The polymer/drug solution (organic phase) was prepared as follows: 1.65 gm of Medisorb 75:25 dl PLGA (Inherent Viscosity, 0.65 dl/g) was dissolved in 70 gm of ethyl acetate. The concentration of polymer in the organic phase was 2.36%. 0.35 gm micronized pig albumin (Sigma, lot #95F-9358) was suspended in the polymer solution by 2×10 seconds of sonication (Tekmar Sonication Disruptor, Model 350 with microtip). A uniform and fine dispersion was produced. The suspension was poured into a 50 ml reactor equipped with an outlet valve at the bottom. Mixing was initiated with a turbine 6-blade propeller at approximately 700 rpm. A peristaltic pump was connected to the outlet of the reactor to pump the organic phase at a rate of 7.0 g/min into the static mixer. Another peristaltic pump was set to feed 350 cs silicone oil (Dow Corning, Lot #HH121209) at a role of 9.0 g/min into the inlet of the static mixer.

The silicone oil flow was started first and the organic phase followed approximately 2–5 seconds later. In a quench tank, 1.2 L of heptane (Chem Pure, Lot #M138KLAP) was stirred at a moderate speed using an air-driven impeller. The outlet line of the static mixer was placed ½" below the surface of the heptane. At completion of transfer of the organic phase through the static mixer, 8–10 g of ethyl acetate was used to flush the remaining organic phase from the mixer. The silicone oil flow was maintained during this rinsing period. The semi-solid microparticles were quenched in heptane for 1.5 hours at room temperature for complete hardening and washing. Microspheres were then collected by vacuum filtration using a Versapor-3000-membrane filter, 3µ pore size (Gelman). The collected microspheres were washed on the filter with 300 ml of fresh heptane and were transferred to a vacuum desiccator for further drying. The process yielded 1.91 g of pig albumin loaded microspheres. Microparticles were mostly spherical and in a 25–200µ (micron) size range.

A second formulation was prepared which showed that a shorter static mixer (½" diameter×6" long) can be used with a lower total flow rate. The organic phase flow rate was 6.5 g/min into the static mixer, as opposed to 7.0 g/min in the first formulation. The silicone oil flow rate was 8.8 g/min, as opposed to 9.0 g/min in the first formulation. However, the ratio of organic phase flow rate to silicone oil flow rate is approximately the same in the second formulation as in the first formulation. The solid yield of this formulation was 90%.

EXAMPLE 12

Preparation of 10.0% Theoretically Loaded rBo Interferon-α Microspheres

A 1.89 g batch of rBo Interferon-α (recombinant bovine Interferon alpha) loaded microparticles was prepared using a ½"×12" static mixer. The concentration of polymer (75:25 dl PLGA dissolved in ethyl acetate) in the organic phase was 2.70%. The protein was dissolved in 0.5 ml of water for injection and was emulsified in the polymer solution by sonication to form the organic phase (polymer/active agent phase). The emulsion was poured into a reactor and the microsphere preparation was performed in like manner to Example 11. The organic phase flow rate was 6.6 g/min and the silicone oil flow rate was 10.9 g/min. The semi-solid microparticles were quenched in 1.0 L of heptane for 1.5 hours.

EXAMPLE 13

Preparation of 17.5% Theoretically Loaded HSA Microspheres

A batch of HSA (human serum albumin) loaded microspheres was prepared using a ½"×6" static mixer. The concentration of polymer (75:25 dl PLGA dissolved in ethyl acetate) in the organic phase was 2.36%. An inner water phase of 1.0 ml was used to completely dissolve the protein. The dissolved protein was emulsified in the polymer solution by sonication to form the organic phase. To maintain the required residence time to induce coacervation by the non-solvent (silicone oil) in a shorter flow path of 6", a lower total flow rate was used. The organic phase flow rate was 4.9 g/min and the silicone oil flow rate was 5.6 g/min. The lower total flow rate resulted in a solids yield of 65% for this sample. The ratio of silicone oil flow rate to organic phase flow rate in this sample was slightly lower than in the sample prepared in Example 12, 1.1 as compared with 1.4. The semi-solid microspheres were quenched in 0.8 L of heptane for 1.5 hours. Since less non-solvent (silicone oil) was used, less heptane (second non-solvent) was required.

EXAMPLE 14

Preparation of 10.0% Theoretically Loaded Pig Albumin Microspheres

This formulation was prepared similar to the one in Example 12, using pig albumin as the model protein (active agent to be encapsulated). The total flow rate of the two phases in the static mixer was lower in this sample; the organic phase flow rate was 6.0 g/min and the silicone oil flow rate was 8.8 g/min. The microspheres were quenched in 1.2 L of heptane for 1.5 hours. A total solids yield similar to Example 13 was achieved for this formulation.

The characteristics of the formulations for Examples 11–14 are summarized in Table 4.

EXAMPLE 15

An 85:15 D,L-lactide/glycolic acid copolymer (10.6 g) and norethindrone USP (9.4 g) were sequentially dissolved in a 50:50 (weight) blend of ethyl acetate and benzyl alcohol (80 g) ("oil phase"). Once dissolved, the solution was transferred to a 500 g emulsion bath mixture at 60°–65° C. composed of 0.5 weight percent poly(vinyl alcohol) (Vinol 205, Air Products, having a number average molecular weight of 15,000 to 27,000 and a degree of hydrolysis of 87–89%), 5.9 weight percent ethyl acetate, 2.7 weight percent benzyl alcohol, and 90.9 weight percent water, contained in a 1000 mL jacketed beaker equipped with a turbine stirrer and a thermostatic heater. This emulsion bath mixture approximated a saturated solution for both ethyl acetate and benzyl alcohol at 60° C. During emulsion formation, extraction of solvent from the "oil phase" can thus be prevented and any time effect during this step minimized. The stir speed was adjusted to provide for an oil droplet size of approximately 90 μm. The resulting emulsion was transferred to a chilled (2°–4° C.) water tank containing various amounts of water and ethyl acetate, as reported in FIGS. 14A–C and 15A–C. After one hour, the microparticles were collected on a sieve stack (25, 45, 63 and 90 μm) and allowed to dry overnight under a hood. The next day the microparticles were blended (15%: 25–45 μm; 50%: 45–63 μm; and 35%: 63–90 μm) and sampled. The results are reported in FIGS. 14A–C and 15A–C.

EXAMPLE 16

Example 15 is repeated except that the size of the "oil phase" solution of NET and polymer is 5 g in each case, the emulsification bath is 300 mL of water containing 0.5 wt % of the poly(vinyl alcohol) used in Example 15. The results are reported in Table 5.

TABLE 4

| Example | Coreload (%) | Protein | Polymer Conc. (%) | H₂O (ml) | Flow-rate (g/min) Organic Ph. | Silicone oil | 2nd non-solvent volume (L) | Period (hr) |
|---|---|---|---|---|---|---|---|---|
| 11 | 17.5 | Pig Albumin | 2.36 | 0 | 7.0 | 9.0 | 0.8 | 1.0 |
| 11 | 17.5 | Pig Albumin | 2.36 | 0 | 6.5 | 8.8 | 0.8 | 1.5 |
| 12 | 10.0 | rBo Interferon-α | 2.70 | 0.5 | 6.6 | 10.9 | 1.0 | 1.5 |
| 13 | 17.5 | HSA | 2.36 | 1.0 | 4.9 | 5.6 | 0.8 | 1.5 |
| 14 | 10.0 | Pig Albumin | 2.70 | 0.5 | 6.0 | 8.8 | 1.2 | 1.5 |

TABLE 5

| Batch No. | Description | Solvent Content (%) | Emulsion Conditions Temp (°C.) | RPM | Time (min) | Quench Vol (l) | Yield (%) Total Recovered | 25–90 μ | Core Load | In Vitro Dissolution | Residual Solvent | Scanning Electron Microscopy |
|---|---|---|---|---|---|---|---|---|---|---|---|---|
| 3151 | Dslvd NET/ 50:50; ETAC:BA | 90.0 | Amb | 230 | 15 | 5 | 57.2 | 46 | .461 | 12% Burst, 60% Release @ 18 hr (unblended sample) | ETAC/BA 0.0003/ 3.77 | Very porous, out of round, inconsistent |
| 3161 | Dslvd NET/ 50:50; ETAC:BA | 84.5 | 37 | 247 | 26 | 5/10 | 60.4 | 35 | .416 | 40% Release @ 18 hr (unblended sample) | 0.83/ 1.5 | Inconsistent, less porous |
| 3181 | Dslvd NET/ 50:50; ETAC:BA | 89.9 | Amb | 226 | 9 | 5/10 | 57.0 | 32 | .456 | No burst, 25% Release @ 18 hr (unblended sample) | 0.51/ 1.99 | Rough surface, inconsistent |
| 3251 | Dslvd NET/ 50:50; ETAC:BA | 80.9 | 60 | 250 | 7 | 5/10 | 61.4 | 29 | .445 | No burst, 18% Release @ 18 hr (unblended sample) | 0.38/ 2.56 | Round, some irreg., more consistent |
| 3261 | Dslvd NET/ 50:50; ETAC:BA | 75.0 | 75 | 199 | 7 | 5/10 | 61.0 | 7.6 | .422 | 7% Burst, 58% Release @ 18 hr (unblended sample) | 0.53/ 2.72 | Round, some porous, less consistent |
| 3301 | Dslvd NET/ 50:50; ETAC:BA | 80.9 | 60 | 250 | 11 | 5 | 72.0 | 49 | .431 | nd | non-det/ 12.3 | nd |
| 3381 | Dslvd NET 50:50; ETAC:BA | 90.1 | 25 | 118 | 17 | 5/10 | 39.2 | 39.2 | .421 | No burst, 20.3% Release @ 18 hr (unblended sample) | 0.37/ 3.06 | Round, somewhat smooth |
| 3391 | Dslvd NET/ 50:50; ETAC:BA | 80.9 | 63 | 220 | 10 | 5/10 | 6.2 | 2.2 | .431 | nd | nd | Round, uneven surface |
| 3401 | Dslvd NET/ 50:50; ETAC:BA | 80.9 | 61 | 234 | 8 | 5/10 | 24.8 | 24.8 | .427 | No burst, 46.1% Release @ 18 hr (unblended sample) | 0.22/ 2.09 | Round, eneven surface |

EXAMPLE 17

A 20 gram batch of testosterone-loaded microparticles was made as follows: 10.8 g of the polymer of Example 15 and 9.2 g of testosterone were dissolved in 67 g of a 75:25 blend of ethyl acetate and benzyl alcohol and heated to approximately 65° C. The solution was then transferred to a 500 g aqueous mixture of 0.5% poly(vinyl alcohol) and 6.5% ethyl acetate in a 1000 mL jacketed glass reaction vessel equipped with a turbine stirrer. Stir speed was adjusted to approximately 245 rpm. After five minutes, the emulsion was transferred to a chilled (0°–4° C.) tank containing 20 liters of water spiked with ethyl acetate at a 5% concentration. After one hour, the microparticles were recovered on a 25 and 150 micron sieve stack and allowed to dry overnight under a laboratory hood. The next day, the microparticles on the 25 micron screen were recovered and sampled. The product contained 39.7% testosterone, 3.67% ethyl acetate, and 0.89% benzyl alcohol. An accelerated in vitro release model indicated 15% of the drug was released after 18 hours in the receiving fluid.

While various embodiments of the present invention have been described above, it should be understood that they have been presented by way of example only, and not limitation. Thus the breadth and scope of the present invention should not be limited by any of the above described exemplary embodiments, but should be defined only in accordance with the following claims and their equivalents.

What is claimed is:

1. A method of preparing microparticles, comprising:
   preparing a first phase, said first phase comprising an active agent and a polymer;
   preparing a second phase;
   preparing a quench liquid; and
   pumping said first phase and said second phase through a static mixer into said quench liquid thereby forming microparticles containing said active agent.

2. The method of claim 1, wherein said first phase and said second phase are substantially immiscible.

3. A method of preparing microparticles, comprising:
   preparing a first phase, said first phase comprising an active agent and a polymer;
   preparing a second phase, wherein said second phase is free from solvents for said polymer;
   preparing a quench liquid; and
   pumping said first phase and said second phase through a static mixer into said quench liquid thereby forming microparticles containing said active agent.

4. The method of claim 2, further comprising:
   configuring said static mixer with a plurality of static mixing elements received within a conduit.

5. The method of claim 2, wherein said pumping step is performed wherein said first phase is pumped at a first flow rate and said second phase is pumped at a second flow rate greater than said first flow rate.

6. The method of claim 2, wherein said step of preparing said first phase further comprises:
   dissolving said active agent in a solution containing said polymer.

7. The method of claim 2, wherein said step of preparing said first phase further comprises:
   preparing a dispersion comprising said active agent.

8. The method of claim 2, wherein said step of preparing said first phase further comprises:
   preparing an emulsion comprising said active agent.

9. The method of claim 2, wherein said step of preparing said first phase further comprises:
   dissolving polylactide-co-glycolide in ethyl acetate to form a polymer solution; and
   dissolving trenbolone acetate in said polymer solution.

10. The method of claim 2, wherein said step of preparing said first phase further comprises:

dissolving polylactide-co-glycolide in ethyl acetate to form a polymer solution; and dissolving testosterone in said polymer solution.

11. The method of claim 2, wherein said step of preparing said first phase further comprises:

dissolving polylactide-co-glycolide in ethyl acetate to form a polymer solution; and dissolving estradiol benzoate in said polymer solution.

12. The method of claim 3, wherein said step of preparing said first phase further comprises:

preparing a dispersion comprising said active agent.

13. The method of claim 3, wherein said step of preparing said first phase further comprises:

dissolving said active agent in an active agent solvent.

14. The method of claim 3, wherein said active agent is hydrophilic.

15. The method of claim 3, wherein said second phase comprises an aqueous solution of an emulsifier.

16. The method of claim 3, wherein said second phase comprises silicone oil.

17. The method of claim 3, wherein said step of preparing said first phase further comprises:

preparing an emulsion comprising said active agent.

18. The method of claim 3, wherein said active agent comprises a protein.

19. The method of claim 3, wherein said active agent comprises human serum albumin.

20. The method of claim 3, wherein said active agent comprises pig albumin.

21. The method of claim 3, wherein said active agent comprises recombinant bovine interferon-alpha.

* * * * *